(12) United States Patent
Christensen et al.

(10) Patent No.: US 10,583,280 B2
(45) Date of Patent: *Mar. 10, 2020

(54) RETENTION FEATURE FOR SOFT INTERFACE CONNECTION

(71) Applicant: Becton, Dickinson and Company, Franklin Lakes, NJ (US)

(72) Inventors: Kelly Christensen, Centerville, UT (US); Venugopal Ghatikar, Salt Lake City, UT (US); Bryan F. Bihlmaier, Provo, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/916,001

(22) Filed: Mar. 8, 2018

(65) Prior Publication Data

US 2018/0264249 A1    Sep. 20, 2018

Related U.S. Application Data

(63) Continuation of application No. 14/064,915, filed on Oct. 28, 2013, now Pat. No. 9,993,634.

(51) Int. Cl.
*A61M 39/10* (2006.01)

(52) U.S. Cl.
CPC ........ *A61M 39/10* (2013.01); *A61M 39/1011* (2013.01); *A61M 2039/1033* (2013.01);
(Continued)

(58) Field of Classification Search
CPC .......... A61M 39/10; A61M 2039/1033; A61M 2039/1038; A61M 2039/1044; A61M 2039/1072; Y10T 29/49826
See application file for complete search history.

(56) References Cited

U.S. PATENT DOCUMENTS 4,461,394 A    7/1984   Sendel et al.
4,770,308 A    9/1988   Lynn
(Continued)

FOREIGN PATENT DOCUMENTS

EP    158030      10/1985
JP    60-129941    8/1985
(Continued)

OTHER PUBLICATIONS

Neutral Under Pressure, The nPulse Valve Platform Brochure, NP Medical, pp. 1-2.
(Continued)

*Primary Examiner* — Lauren P Farrar
(74) *Attorney, Agent, or Firm* — Kirton & McConkie; Craig Metcalf; Kevin Stinger

(57) ABSTRACT

A retention feature configured to provide interference between a threaded connection of a Luer access device and a separate device, wherein the Luer access device further comprises a septum that provides a soft interfaced between the two threadedly connected devices. The retention features of the instant invention are designed to provide the user with a tactile sensation of a tightening threaded connection, despite a soft interface between the interconnected devices. The retention features of the instant invention further prevent "spring back" and unintentional disengagement of the interconnected devices.

3 Claims, 24 Drawing Sheets

(52) U.S. Cl.
CPC ............... *A61M 2039/1038* (2013.01); *A61M 2039/1044* (2013.01); *A61M 2039/1072* (2013.01); *Y10T 29/49826* (2015.01)

(56) References Cited

U.S. PATENT DOCUMENTS

| | | | |
|---|---|---|---|
| 5,462,186 | A | 10/1995 | Ladina et al. |
| 6,152,913 | A | 11/2000 | Feith et al. |
| 6,224,588 | B1 * | 5/2001 | Jentzen ................. A61M 5/347 604/241 |
| 6,908,459 | B2 | 6/2005 | Harding et al. |
| 7,314,061 | B2 * | 1/2008 | Peppel ................. A61M 39/02 137/605 |
| 7,645,414 | B2 | 1/2010 | Gregory et al. |
| 8,777,931 | B2 | 7/2014 | Davis et al. |
| 2003/0208165 | A1 * | 11/2003 | Christensen ........ A61M 39/045 604/256 |
| 2005/0197646 | A1 | 9/2005 | Connell et al. |
| 2006/0089603 | A1 | 4/2006 | Truitt et al. |
| 2006/0213563 | A1 | 9/2006 | Peppel |
| 2008/0287920 | A1 | 11/2008 | Fangrow et al. |
| 2014/0339811 | A1 | 11/2014 | Wong |

FOREIGN PATENT DOCUMENTS

| | | |
|---|---|---|
| JP | 2003-072793 | 3/2003 |
| JP | 2005-110842 | 4/2005 |
| JP | 2013-523222 | 6/2013 |
| WO | 2008/058135 | 5/2008 |
| WO | 2012/105892 | 8/2012 |

OTHER PUBLICATIONS

Ultrasite, Needle-free IV System Brochure, B. Braun Medical Inc., pp. 1-2.
Caresite, Luer Access Device Brochure, B. Braun Medical Inc., pp. 1-2.
V. Link, Luer Activated Device Brochure, Baxter Healthcare Corporation, pp. 1-2.
Clearlink, Needleless IV Access System Brochure, Baxter Healthcare Corporation, pp. 1-2.

* cited by examiner

RETENTION FEATURE FOR SOFT INTERFACE CONNECTION

RELATED APPLICATIONS

This application is a continuation of U.S. application Ser. No. 14/064,915, filed Oct. 28, 2013, titled RETENTION FEATURE FOR SOFT INTERFACE CONNECTION, which is incorporated herein in its entirety.

BACKGROUND OF THE INVENTION

The present invention relates generally to features and devices to improve a threaded connection between two or more devices, wherein a soft interface is provided between the devices. In particular, the present invention relates to a retention feature that is configured to interfere with a threaded connection, wherein the presence of the retention feature provides increased frictional force between the threads of the threaded devices, thereby increasing the force required to disengage the devices and providing the user with tactile feedback which indicates a status of the threaded connection.

Traditional threaded conical or Luer fittings utilize a 6% Luer taper on opposing surface of the connectors to be threadedly connected. As the threads of the connectors are rotated relative to each other, the male and female conical surface are driven and wedged together, thereby forming a secure and fluid-tight connection. Most often this type of traditional connection is best accomplished when the male and female conical surfaces are either non-compliant or equally compliant, such that the opposing surfaces are able to achieve a secure fit. When tightening these surfaces, friction between the male and female conical surfaces provides resistance to disengaging the devices and further provides the user with a tactile sensation or feedback which indicates a complete and secure connection has been achieved.

With reference to FIGS. 1 and 2, a depiction of a PRIOR ART vascular access device 10 is shown. Generally, a vascular access device 10 is used to introduce a substance via a catheter 12 across the skin 14 and into a blood vessel 16 of a patient 18. The vascular access device 10 typically includes a body 20 with a lumen or opening 34 and a soft septum 22 placed within the opening. The vascular access device 10, including the body 20 and the septum 22, may comprise various structural and design modifications, as are presently known in the art.

In some examples, soft septum 22 has a slit 24 through which a separate extravascular device 26, such as a syringe, may introduce a substance into the vascular access device 10. A syringe is one exemplary separate device 26. Other suitable known extravascular devices may include additional vascular access devices, IV administration sets, a male Luer adapter, or other common or yet to be developed medical devices.

A vascular access device 10 may be combined with various other intravenous components to form a larger extravascular system 28. As part of operating the extravascular system 28, a tip 30 of the separate device 26 may be inserted into the vascular access device 10 through slit 24 of soft septum 22. The tip 30 penetrates the device 10 separating at least portions of the two opposing slit surfaces of septum 22. Septum 22 and slit 24 may be configured to seal, or at least substantially seal, around tip 30 as it is inserted into the vascular access device 10. Accordingly, the surfaces near the slit ends may not be separated until the tip 30 is sufficiently inserted into vascular access device 10. The tip 30 serves to open the slit 24 to allow fluid to pass through the device 10, into the catheter 12, and out the end 32 of the catheter when the device is in use.

Generally, the body 20 of vascular access device 10, and separate device 26 comprises a rigid or semi-rigid polymer material, such as polycarbonate or polypropylene. Septum 22 generally comprises a soft, pliable, resilient material, such as silicon or polytetrafluoroethylene. Thus, when separate device 26 is inserted through slit 24 of septum 22, septum 22 provides a soft, pliable barrier between the rigid or semi-rigid materials of separate device 26 and body 20. Although the interface between septum 22 and separate device 26 is secure and fluid-tight, the non-compliant material of separate device 26 and compliant material of septum 22 may reduce the security of the connection and reduces the desired tactile feedback to the user that is experienced with traditional Luer connections. Thus, the user may be unsure of the security of the connection which may result in the connection being over-tightened or unnecessarily examined.

In some instances, the act of threadedly coupling separate device 26 to body 20 causes an exposed portion of septum 22 to become pinched between separate device 26 and body 20. The resilient properties of septum 22 cause a "spring back" effect between the two threaded components, wherein separate device 26 may become partially unthreaded from body 20 following tightening. This "spring back" effect may further reduce the security of the connection and provide a dissatisfying tactile sensation to the user, wherein the soft interface of septum 22 prevents the user from sensing a progression of tightening between separate device 26 and body 20. The user therefore may lack confidence in the connection and may attempt to over-tighten the components, as discussed previously.

Thus, while techniques currently exist that are used for interconnecting threaded devices, challenges still exist. Accordingly, it would be an improvement in the art to augment or even replace current techniques with other techniques.

BRIEF SUMMARY OF THE INVENTION

The present invention relates generally to features and devices to improve a threaded connection between two or more devices, wherein a soft interface is provided between the devices. In particular, the present invention relates to a retention feature that is configured to interfere with a threaded connection, wherein the presence of the retention feature provides increased frictional force between the threads of the threaded devices, thereby increasing the security of the connection and providing the user with tactile feedback which indicates a status of the threaded connection. In some instances, the retention feature provides the user with a tactile sensation that indicates that the threaded connection is progressively or gradually tightening.

In some implementations, a retention feature is provided to prevent "spring back" from occurring due to a soft interface between the threadedly coupled devices. For example, a retention feature may be provided which increases frictional force between the threads of the device and the retention feature, thereby interlocking the threaded surfaces. In other instances, a retention feature is provided comprising a non-compliant material, wherein the compliant material of one or more of the threadedly interconnected devices is temporarily deformed by the presence of the retention feature, thereby increasing the frictional force between the sets of engaged threads. Further, in some instances a retention feature is provided comprising a compliant material, wherein the non-compliant material of one or more of the threadedly interconnected devices temporarily deforms the retention feature when contacted, thereby increasing the frictional force between the retention device and the threads. The act of deforming the retention feature may also increase the friction force between the set of interconnected threads.

Some implementations of the instant invention provide a Luer access device comprising a body having an outer surface. The Luer access device further includes an opening formed in the outer surface and configured to receive a separate device, such as a needleless connector. The Luer access device further includes a soft septum disposed in the opening and having a slit for receiving the separate device. The Luer access device further includes a set of threads positioned on the outer surface of the device and in proximity to the opening of the device. Further still, the Luer access device comprises a retention feature that is disposed on the body at a position adjacent the set of threads, and positioned to contact a portion of a complementary set of threads of the separate device when threadedly coupled to the set of threads of the Luer access device. When contact is made between the complementary threads and the retention feature, tactile feedback is provided to a user which indicates a tightened connection between the Luer access device and the separate device, and an increased force necessary to disconnect the devices is produced to prevent unintentional disengagement of the separate device from the Luer access device.

In some instances, the retention feature comprises a protrusion. The retention feature may be positioned at any location on the Luer access device. In some instances, the retention feature is positioned between an upper thread and a lower thread of the Luer access device's set of threads. In other instances, the retention feature comprises a first end that abuts the lower thread, and further comprises a second end that abuts the upper thread. The retention feature may further comprise an axial taper, wherein a surface of the retention feature tapers outwardly from a base of the feature to a top of the feature. For example, in some instances the second end of the retention feature comprises a protrusion height that is greater than a protrusion height of the first end, such that the retention feature tapers inwardly from the second end to the first end.

The retention feature may further comprise a ramped configuration, wherein the second end of the retention feature comprises a protrusion height that is greater than a protrusion height of the first end, such that the ramped protrusion tapers inwardly from the second end to the first end. The retention feature may further comprise a forward leading ramped surface and a rearward or trailing ramped surface, wherein the ramped surfaces taper outwardly from the body of the Luer access device to an apex of the retention feature. In some instances, the apex is symmetrical. In other instance, the apex is asymmetrical wherein the apex comprises a first width that is greater than a second width to provide an axial taper that forms an interface with the forward ramped surface. Further, some implementations of the instant invention provide a retention feature having a forward ramped surface comprising a first angle of incline, and a rearward ramped surface comprising a second angle of incline, wherein the second angle of incline is greater than the first angle of incline.

The present invention further provides a method for manufacturing a Luer access device, the method including steps for: 1) providing a body having an outer surface; 2) forming an opening in the outer surface of the body, the opening being configured to receive a separate device, such as a needleless connector; 3) disposing a soft septum into the opening, the soft septum having a slit for receiving the needleless connector; 4) providing a set of threads of the outer surface and positioned proximate to the opening, a portion of the body being adjacent the set of threads; and 5) disposing a retention feature on the portion of the body adjacent the set of threads, wherein the retention feature is positioned to contact a portion of a complimentary set of threads on the needleless connector when threadedly coupled to the set of threads and provide both resistance to disconnection and provide a tactile feedback to a user of a tightening connection between the Luer access device and the needleless connector.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Figure 1:
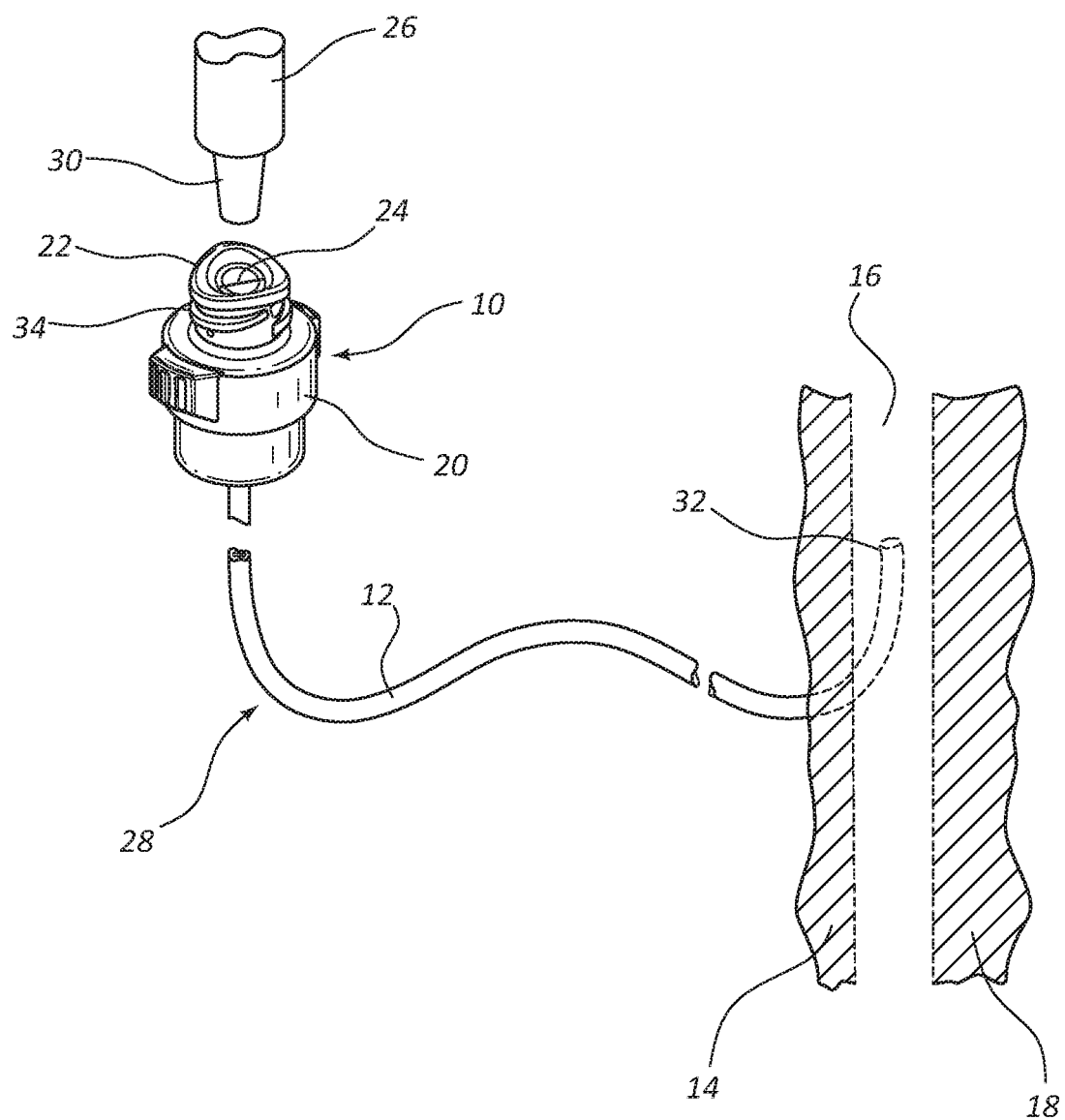
FIG. 1 show a perspective view of a PRIOR ART Luer access device as part of an intravenous system.
Figure 2:
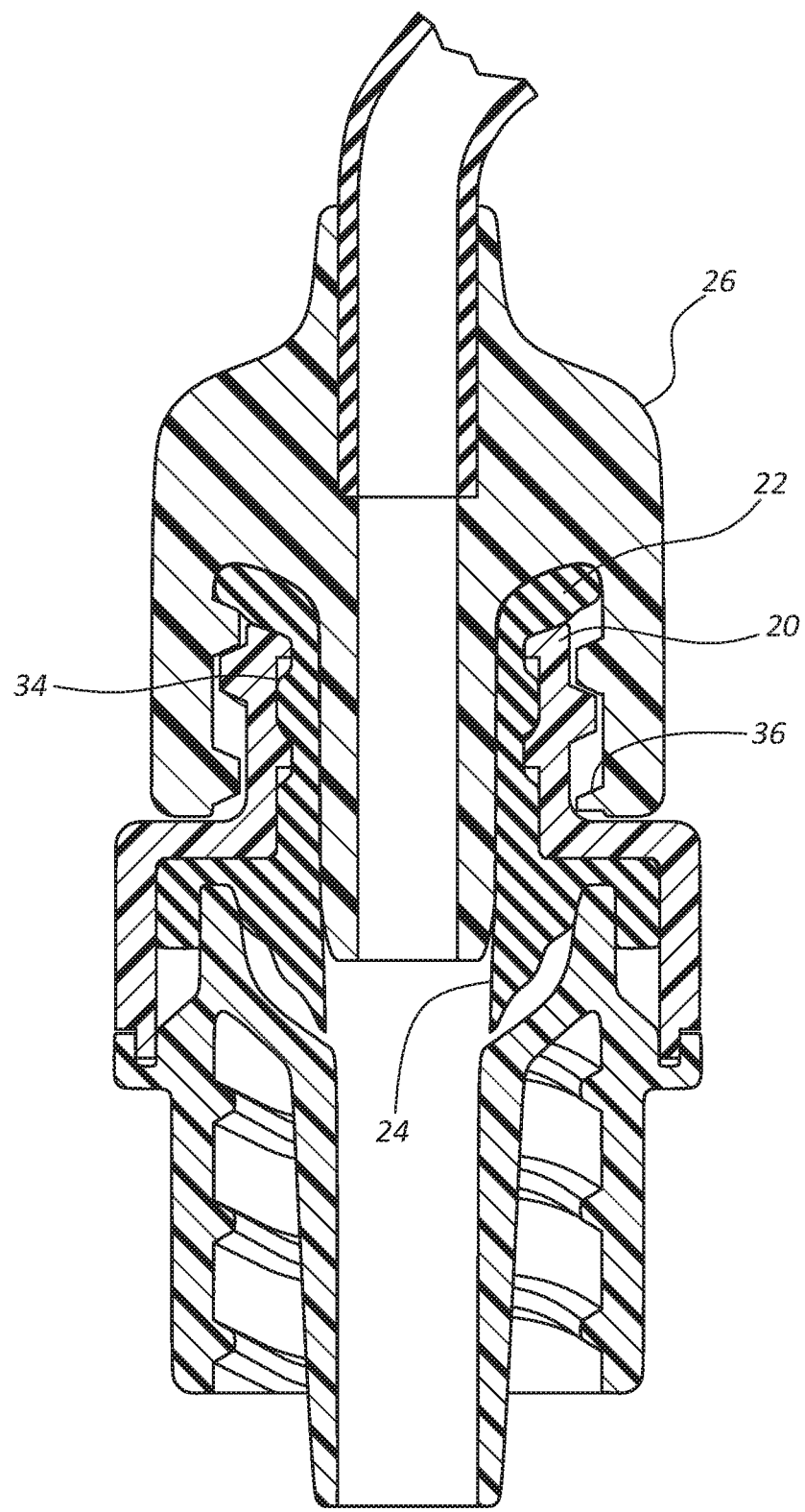
FIG. 2 shows a cross-section view of a PRIOR ART separate device coupled to a PRIOR ART Luer access device as part of an intravenous system.

It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure, but is merely a representative of exemplary combinations of the components.

As used herein, the term "needleless connector" is used to denote a medical coupler which is used as part of an intravenous assembly. In some instances, a needleless connector comprises a Luer adapter. In other instances, a needleless connector comprises a PRN connector. An example of a needleless connector is the Q-Syte™ luer access port from Becton, Dickinson. Further, in some instances a needleless connector comprises a port or valve of a section of intravenous tubing or a connector thereof. One having skill in the art will appreciate that the systems and methods of the present invention may be adapted for use with various other types of connectors and other devices for which automated disinfection is desirable.

Referring now to FIG. 3, a Luer access device 100 in accordance to a representative embodiment of the present invention is shown. Luer access device 100 may comprise any general structure or design that is presently known in the art. For example, in some instances Luer access device 100 comprises cap structure as shown in FIG. 3A. Luer access device 100 may alternatively comprise a male Luer device, as shown in cross-section in FIG. 3B. Luer access device 100 may further comprise an access port structure that is part of an intravenous connector.

Luer access device 100 comprises a body 120 made from a rigid or semi-rigid material having an opening 134 into which is seated a soft septum 122. Body 120 further comprises a set of threads 140 that is positioned on the outer surface of body 120 and in proximity to opening 134. Threads 140 are provided to facilitate a threaded connection between Luer access device 100 and a separate device 26, such as a syringe, a Luer adapter, a cap, or a section of intravenous tubing. In some instance, threads 140 comprises a plurality of partial threads that occupy a portion of the outer surface of body 120, wherein the partial threads each have a thread length that is less than the circumference of the outer surface on which the threads are positioned.

Luer access device 100 further comprises a retention feature 150 that is positioned on body 120 adjacent the set of threads 140. In general, retention feature 150 is positioned on body 120 such that retention feature 150 will contact a set of complementary threads on the separate device 26 when the separate device 26 is threadedly coupled to Luer access device 100 via threads 140. Accordingly, the specific location of retention feature 150 may vary and still accomplish its intended purpose.

Figure 3A:
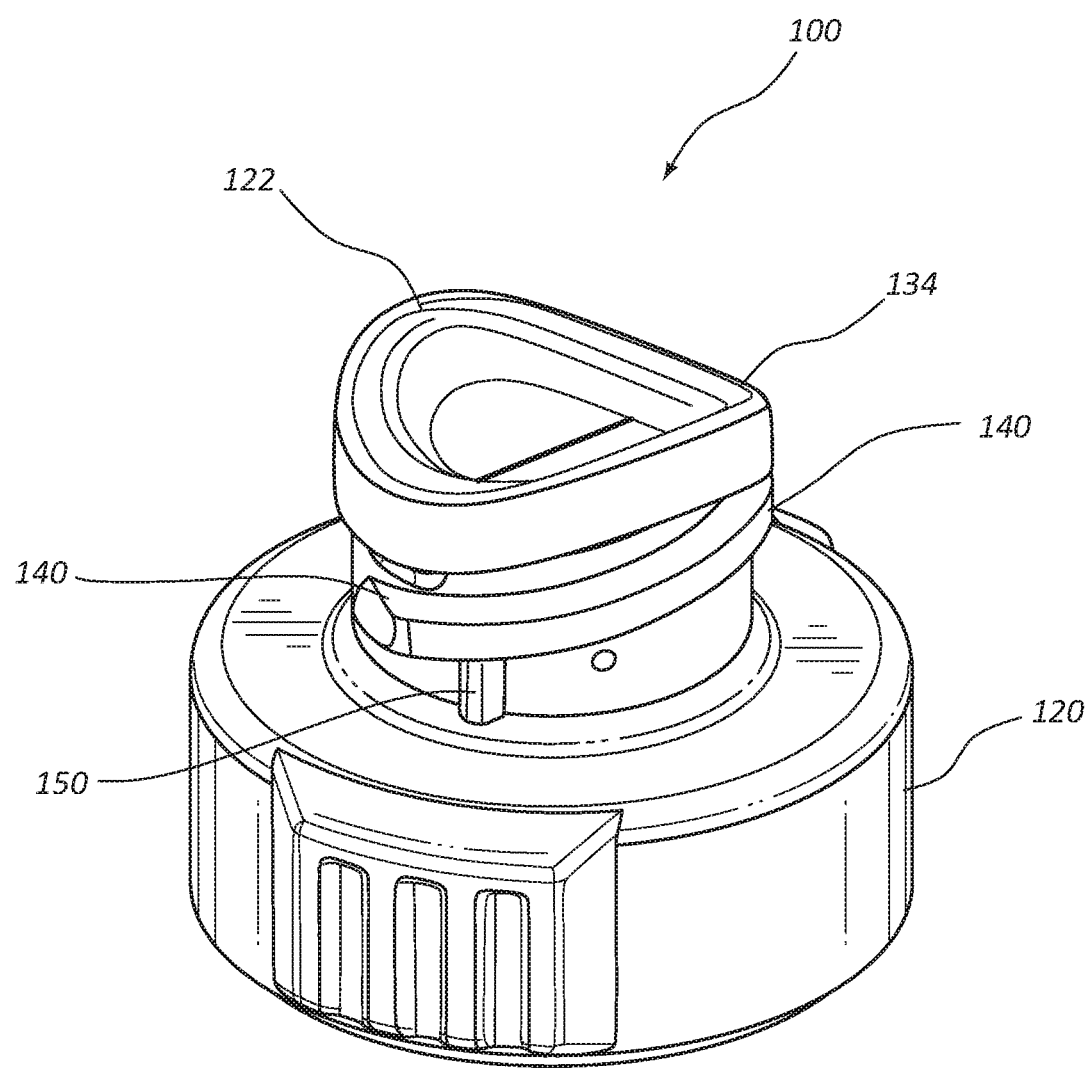
FIG. 3A is an upper perspective view of a Luer access device having a retention feature in accordance with a representative embodiment of the present invention.
Figure 3B:
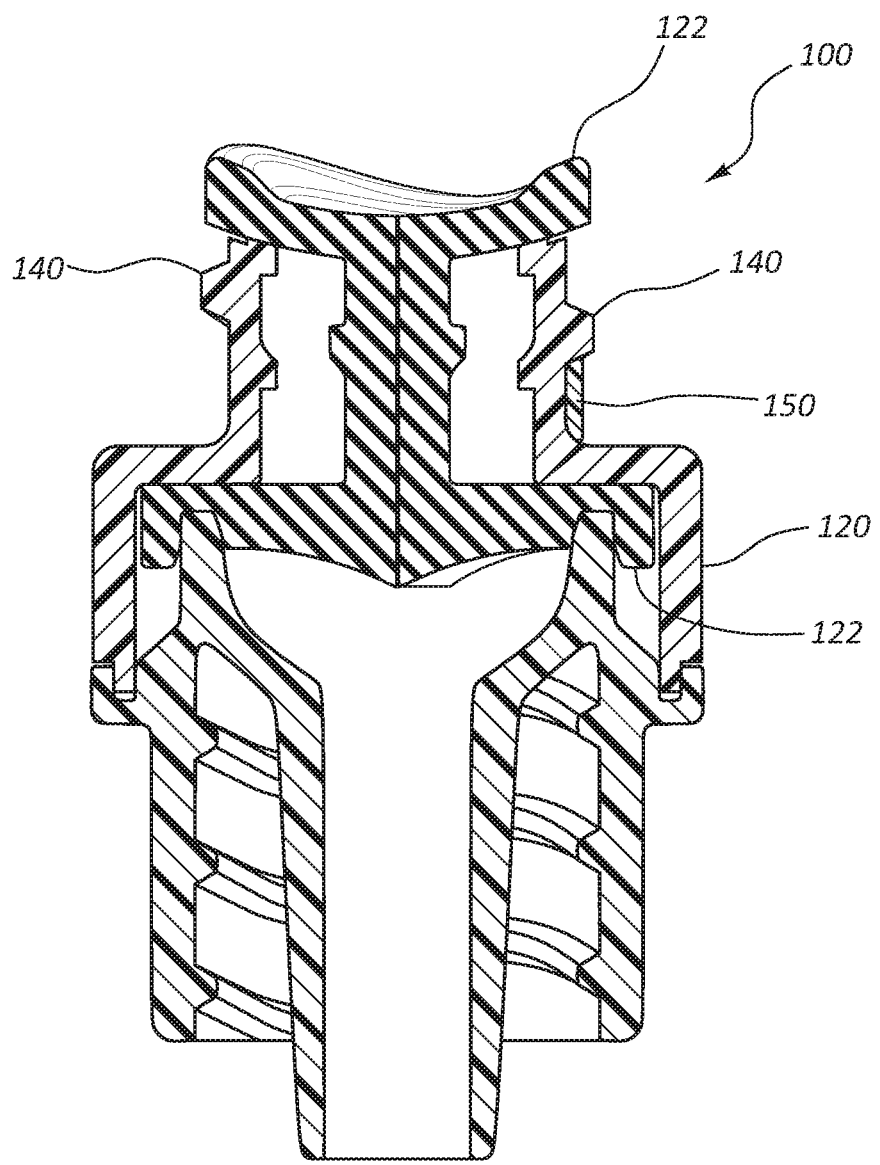
FIG. 3B is a cross-sectional view of the Luer access device of FIG. 3A, in accordance with a representative embodiment of the present invention.

For example, in some instances retention feature 150 is positioned below thread 140 at a position near the middle or end of the thread, as shown in FIGS. 3A and 3B. As thus configured, the complementary threads of separate device 26 are able to engage threads 140 prior to contacting retention feature 150. As separate device 26 is further threaded onto threads 140, the complementary threads of separate device 26 contact retention feature 150 thereby providing a tactile sensation to the user of a tightening connection between the two components. Contact between the complementary set of threads and retention feature 150 further provided increased friction between the threaded components, thereby overcoming the "spring back" effect caused by soft septum 122.

Retention feature 150 may comprise any shape, configuration, texture or other feature that is compatible with the teachings of the present invention. In some instances, retention feature 150 comprises a protrusion that provides an obstacle in the pathway for a set of complementary threads that is intended to threadedly engage threads 140.

Figure 3C:
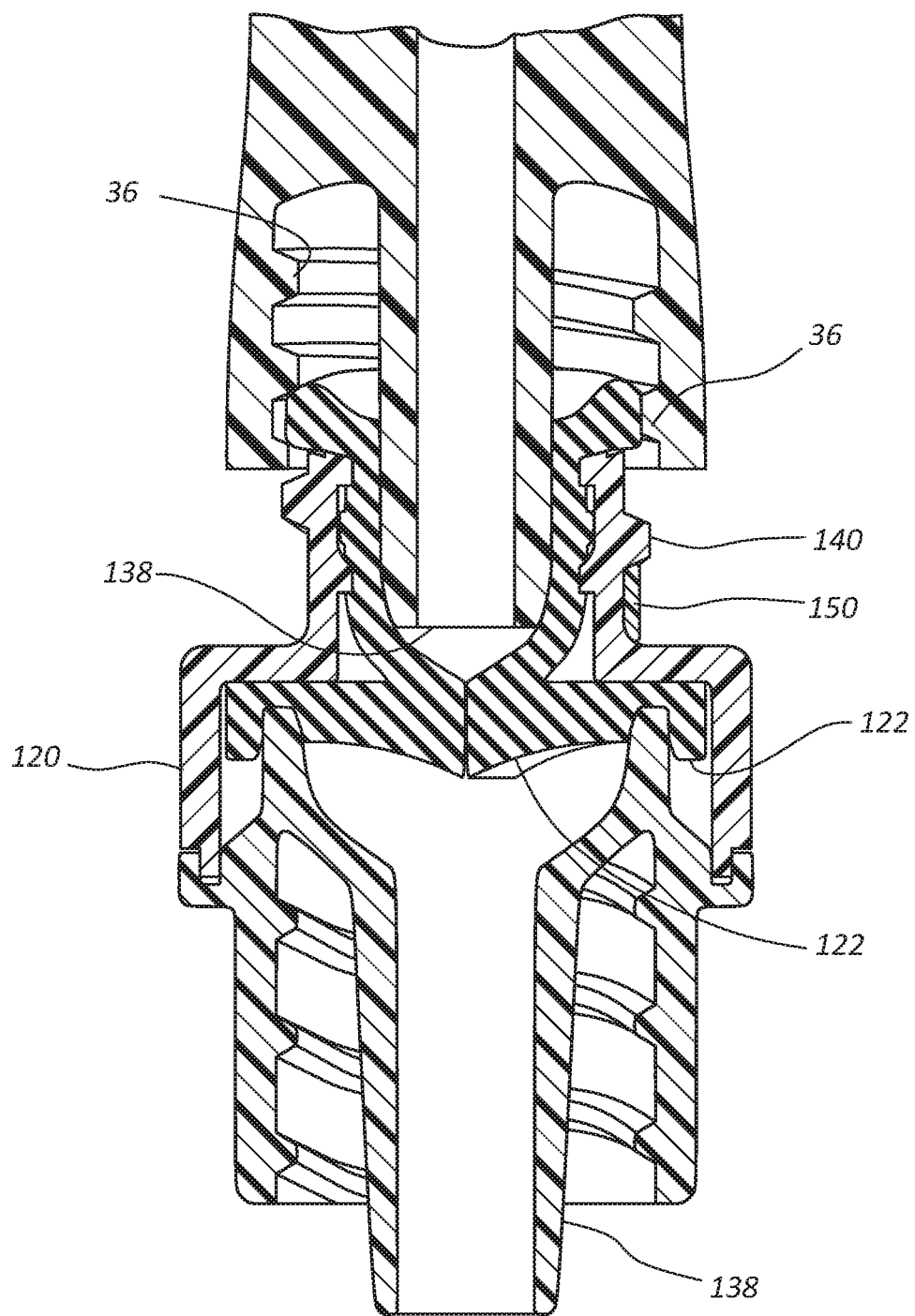
FIG. 3C is another cross-sectional view of the Luer access device of FIG. 3A, illustrating an example separate device piercing an example septum, in accordance with a representative embodiment of the present invention.
Figure 3D:
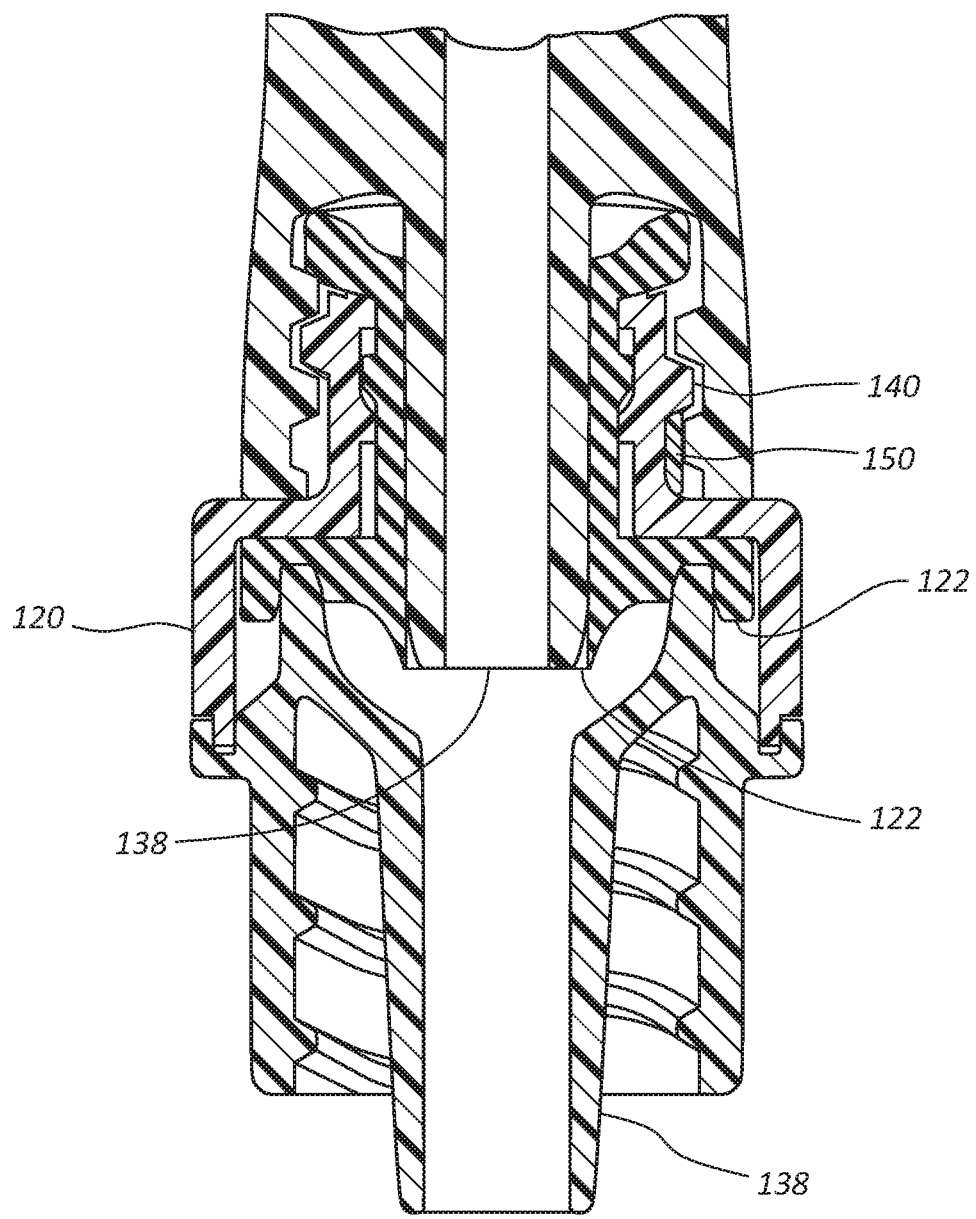
FIG. 3D is another cross-sectional view of the Luer access device of FIG. 3A, illustrating the separate device and the Luer access device engaged, in accordance with a representative embodiment of the present invention.

For example, retention feature 150 may be positioned in proximity to threads 140 so as to be in the pathway of a set of complementary threads of a separate extravascular device. As separate device 26 is initially threaded onto threads 140 of Luer access device 100, a probe 138 portion of separate device 26 pierces septum 122, as shown in FIG. 3C. In some instances, as probe 138 is advanced through septum 122, complementary threads 36 do not immediately make contact with retention feature 150. Rather, threads 140 and complementary threads 36 are permitted to freely and fluidly engage. However, upon further engagement between complementary threads 36 and threads 140, complementary threads 36 contact retention feature 150 as separate device 26 and Luer access device 100 near complete, threaded engagement, as shown in FIG. 3D.

The contact and interaction between complementary threads 36 and retention feature 150 provides a change in the mechanics of the threaded connection. In some instances, this change requires increased rotational torque by the user to complete the threaded connection between the two components. In other instances, this change further provides increased friction between the two components, which can be felt by the user as the connection is tightened. Accordingly, retention feature 150 overcomes the "spring back" effect of soft septum 122, improving security of the connection while simultaneously provided the user with a desirable tactile feedback that confirms tightening of the connection.

Figure 3E:
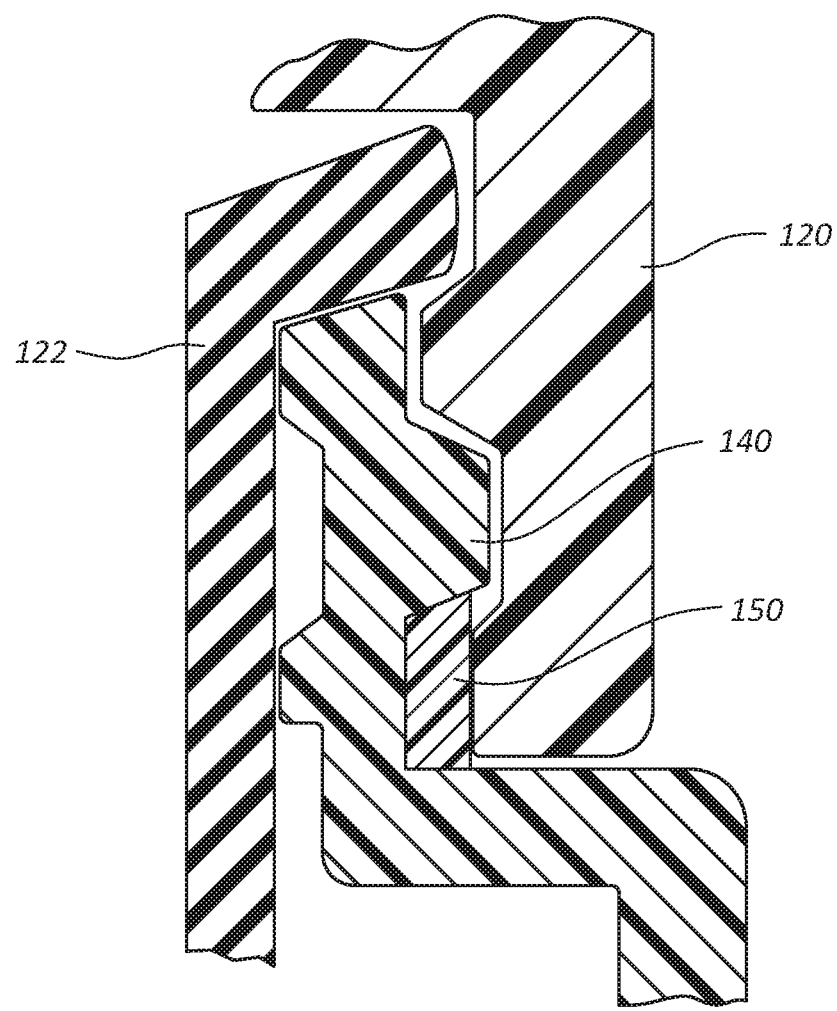
FIG. 3E is a cross-sectional view of a portion of the Luer access device of FIG. 3A, illustrating the separate device and the Luer access device engaged, in accordance with a representative embodiment of the present invention.

In some instances, the complementary threads of separate device 26 comprises a compliant material that is temporarily or permanently deformed when the complementary threads of the device 26 contact retention feature 150, as shown in FIG. 3E. The contact between the complementary threads and retention device 150 may temporarily or permanently misshape the inner diameter of separate device 26, or the shape of complementary threads, thereby increasing the rotational force required to continue coupling separate device 26 and Luer access device 100.

Figure 3F:
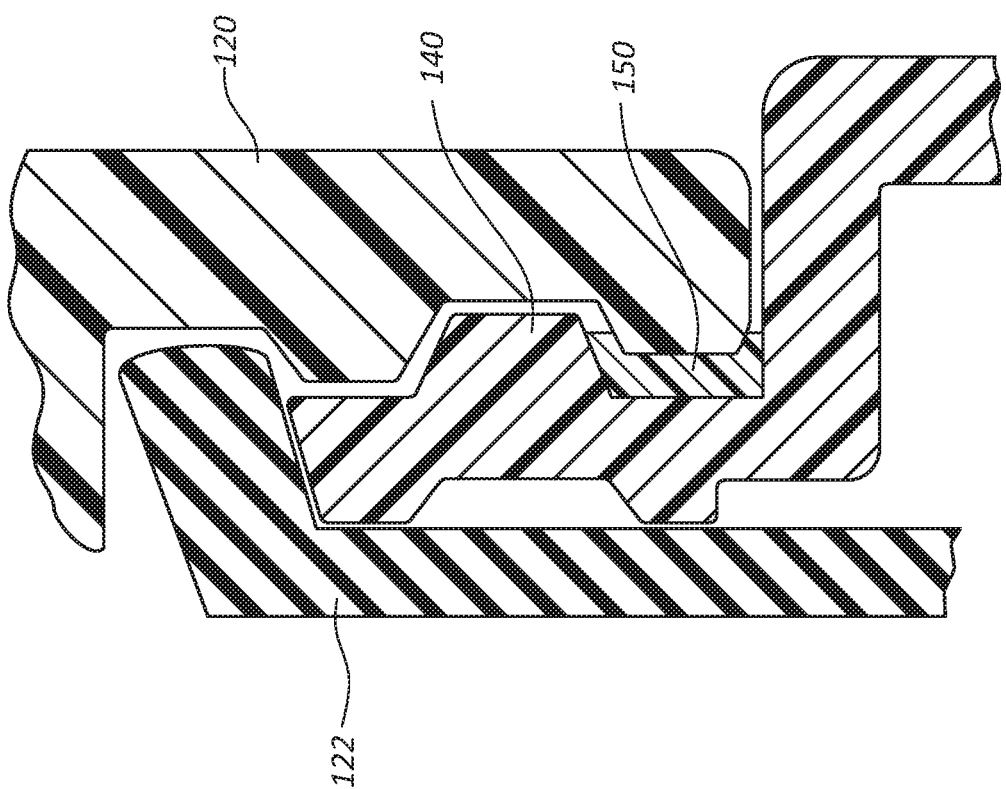
FIG. 3F is another cross-sectional view of a portion of the Luer access device of FIG. 3A, illustrating the separate device and the Luer access device engaged, in accordance with a representative embodiment of the present invention.

Conversely, in some instances retention feature 150 comprises a compliant material that is temporarily or permanently deformed when the noncompliant complementary threads of device 26 contact retention feature 150, as shown in FIG. 3F. The complementary threads of device 26 cut into retention feature 150, thereby increasing friction between the two components.

Figure 3G:
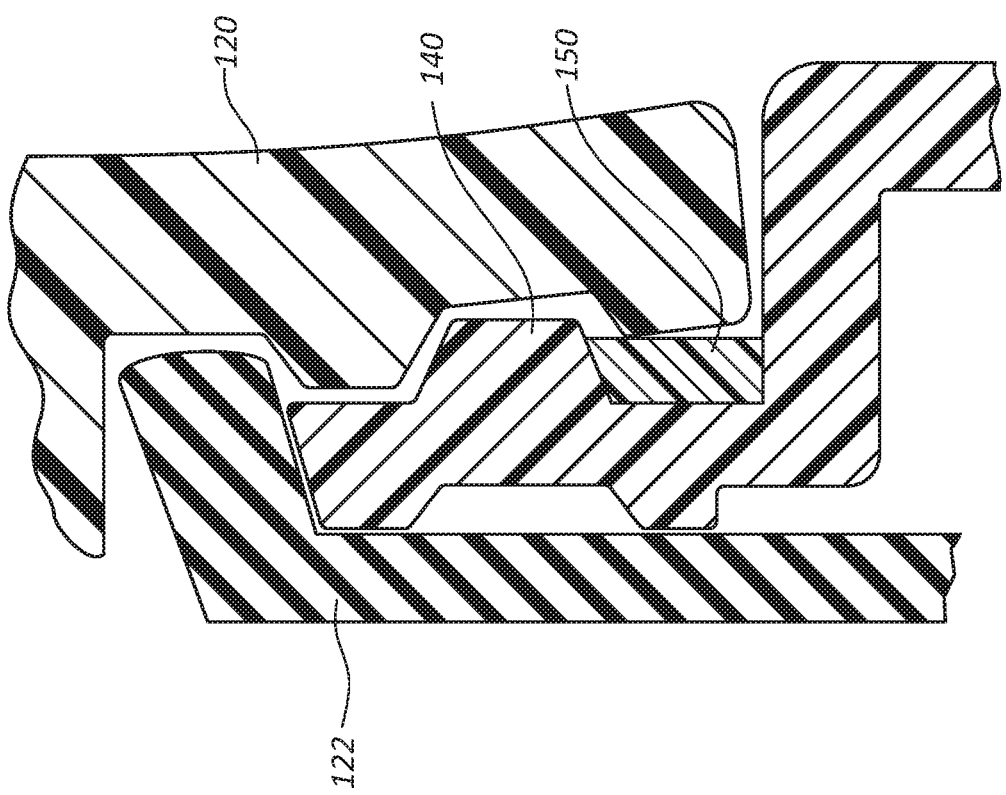
FIG. 3G is another cross-sectional view of a portion of the Luer access device of FIG. 3A, illustrating the separate device and the Luer access device engaged, in accordance with a representative embodiment of the present invention.

Further still, in some instances body 120 comprises a compliant material that is temporarily deformed when contact is made between separate device 26 and retention feature 150, as shown in FIG. 3G. For example, in some instances a noncompliant interface between the complementary threads 36 and retention feature 150 displaces or deflects complementary threads 36 outwardly, thereby increasing the rotational torque required to complete the threaded connection between Luer access device 100 and separate device 26.

Figure 4A:
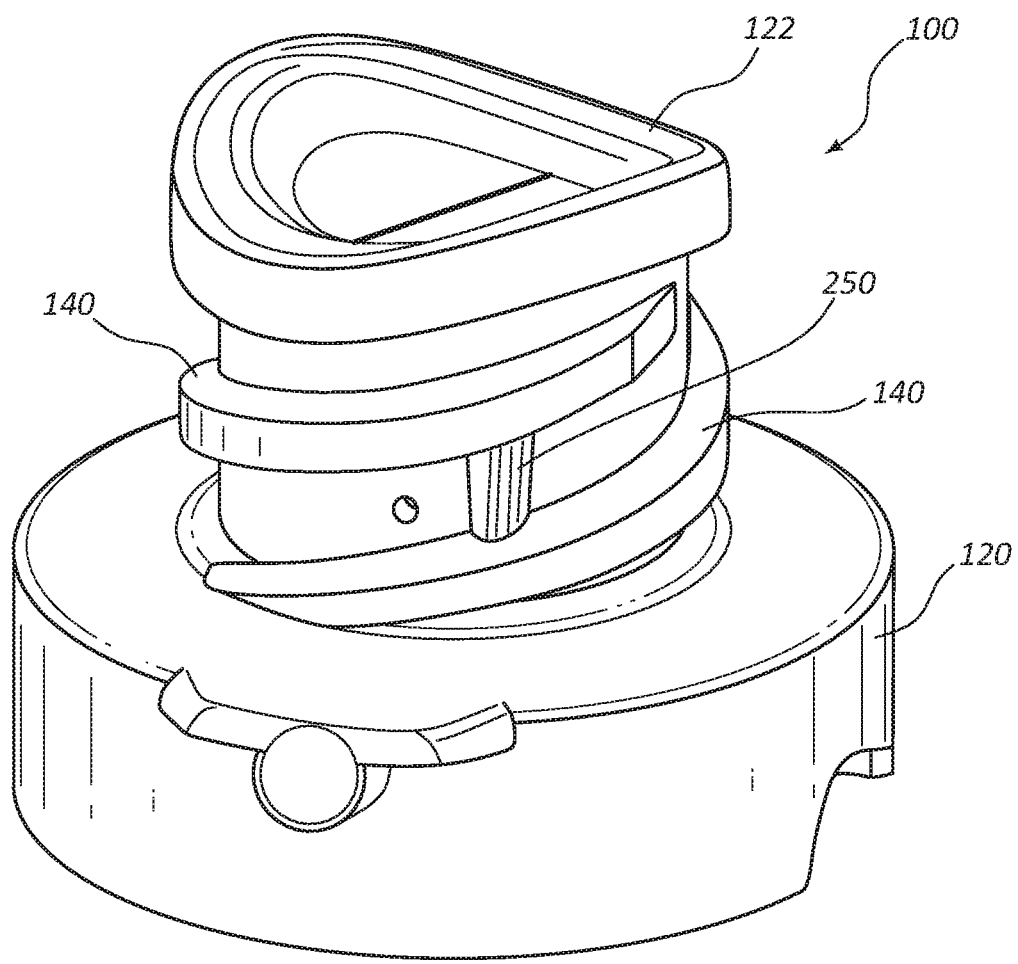
FIG. 4A is an upper perspective view a Luer access device having a tapered retention feature in accordance with a representative embodiment of the present invention.
Figure 4B:
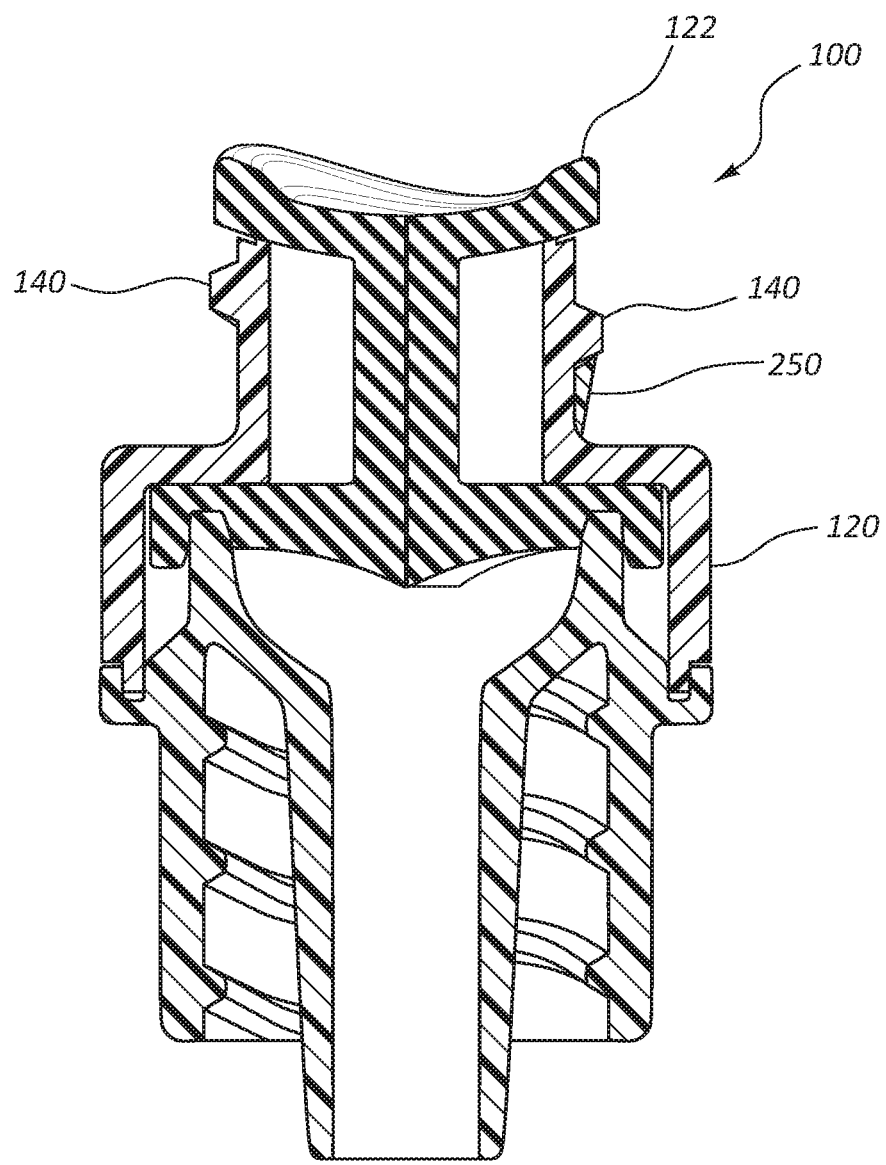
FIG. 4B is a cross-sectional view of the Luer access device of FIG. 4A, in accordance with a representative embodiment of the present invention.
Figure 4C:
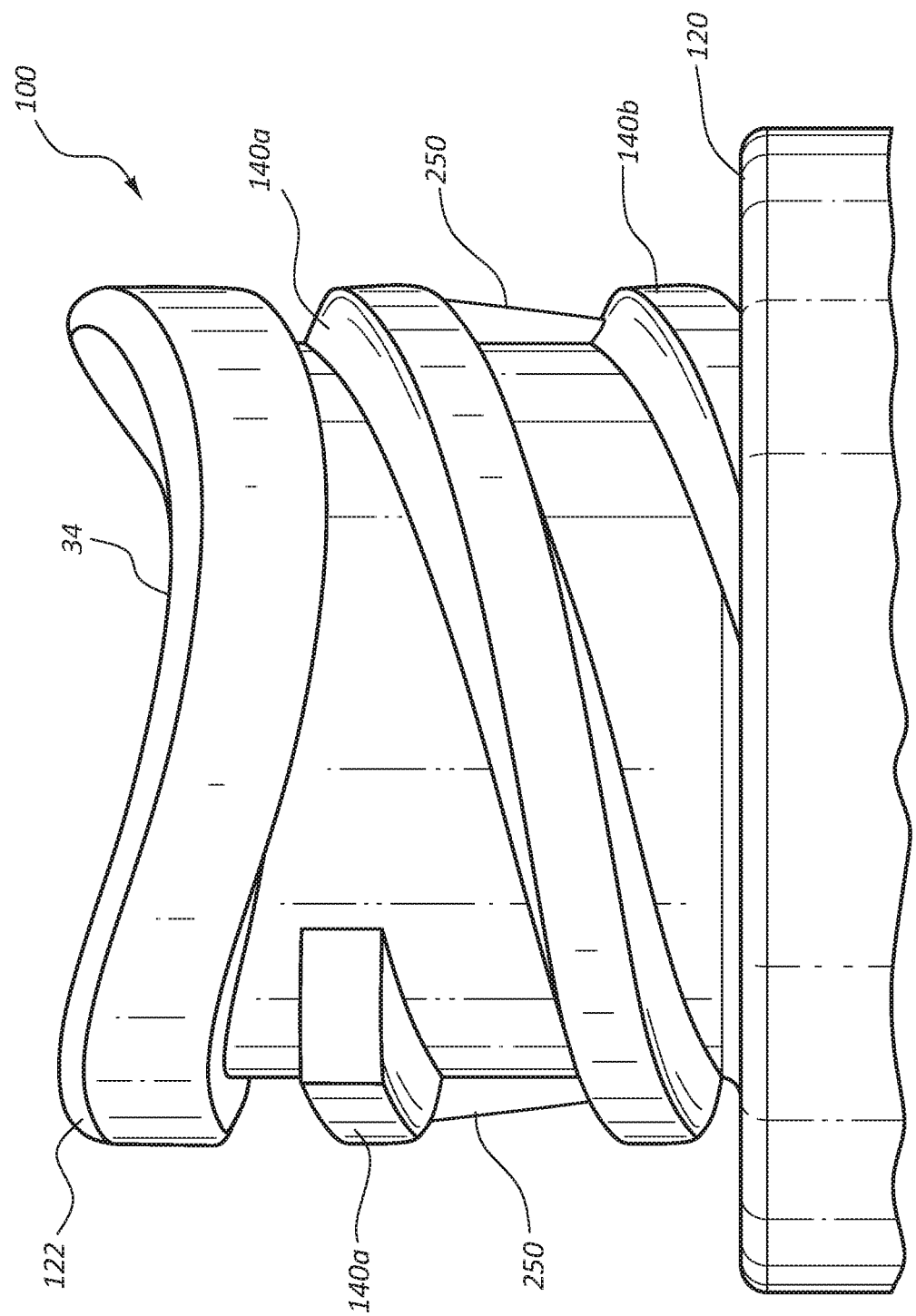
FIG. 4C is a side view of a portion of the Luer access device of FIG. 4A, in accordance with a representative embodiment of the present invention.

Referring now to FIGS. 4A-4C, Luer access device 100 may further comprise a tapered retention feature 250. In some instances, Luer access device 100 comprises a single tapered retention feature 250 that is positioned beneath a set of threads 140 of body 120, as shown in FIGS. 4A and 4B. In other embodiments, Luer access device 100 comprises one or more tapered retention features 250 that are interposedly positioned between an upper thread 140a and a lower thread 140b on body 120, as shown in FIG. 4C. Retention feature 250 tapers inwardly from upper thread 140a to lower thread 140b, such that retention feature 250 comprises an upper thickness that tapers to a lower thickness, wherein the lower thickness is less than the upper thickness.

Figure 5A:
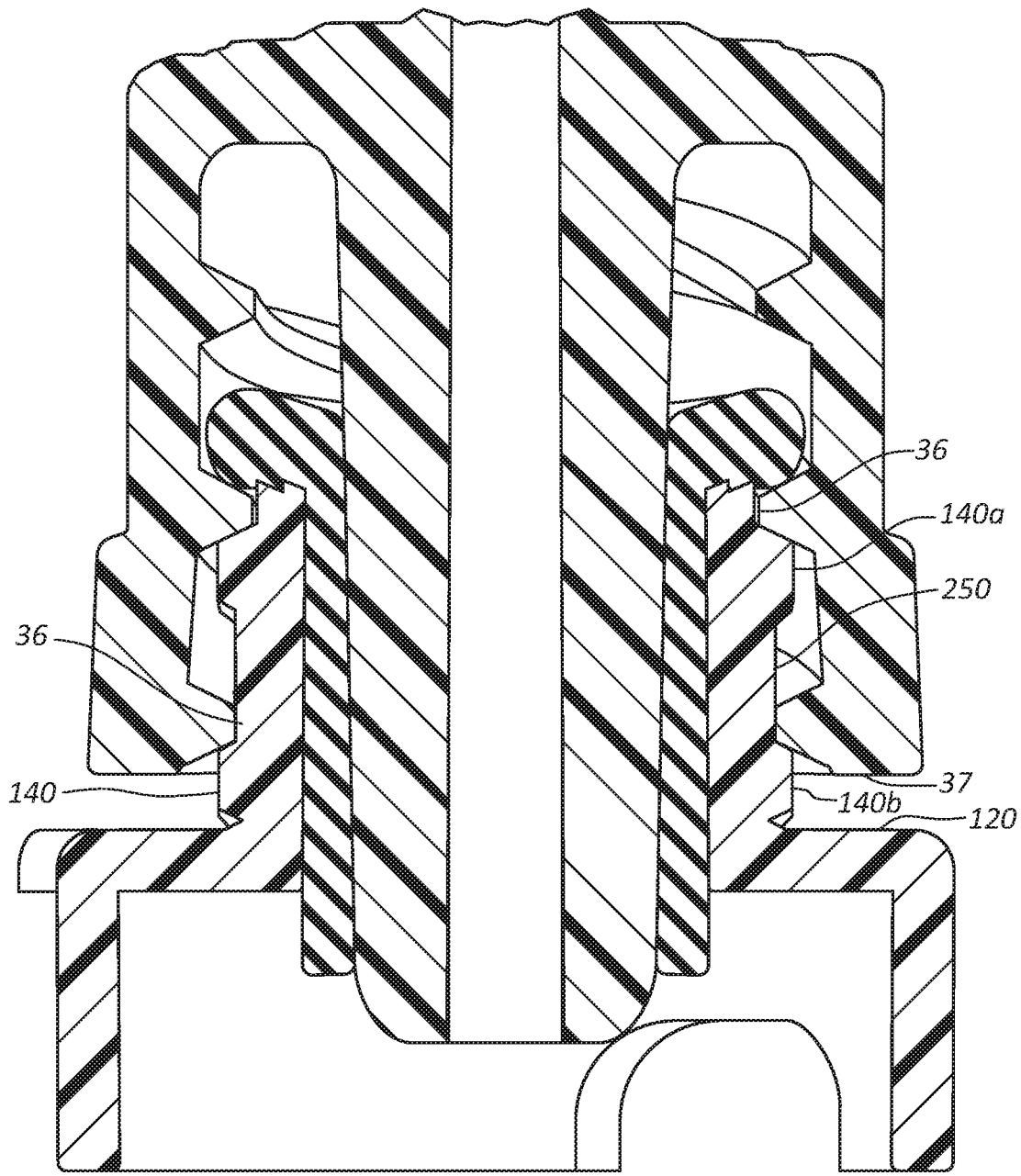
FIG. 5A shows a cross section view of the tapered retention feature of FIG. 4, and demonstrates the operation of tightening a threaded connection between the Luer access device and a separate device in accordance with a representative embodiment of the present invention.
Figure 5B:
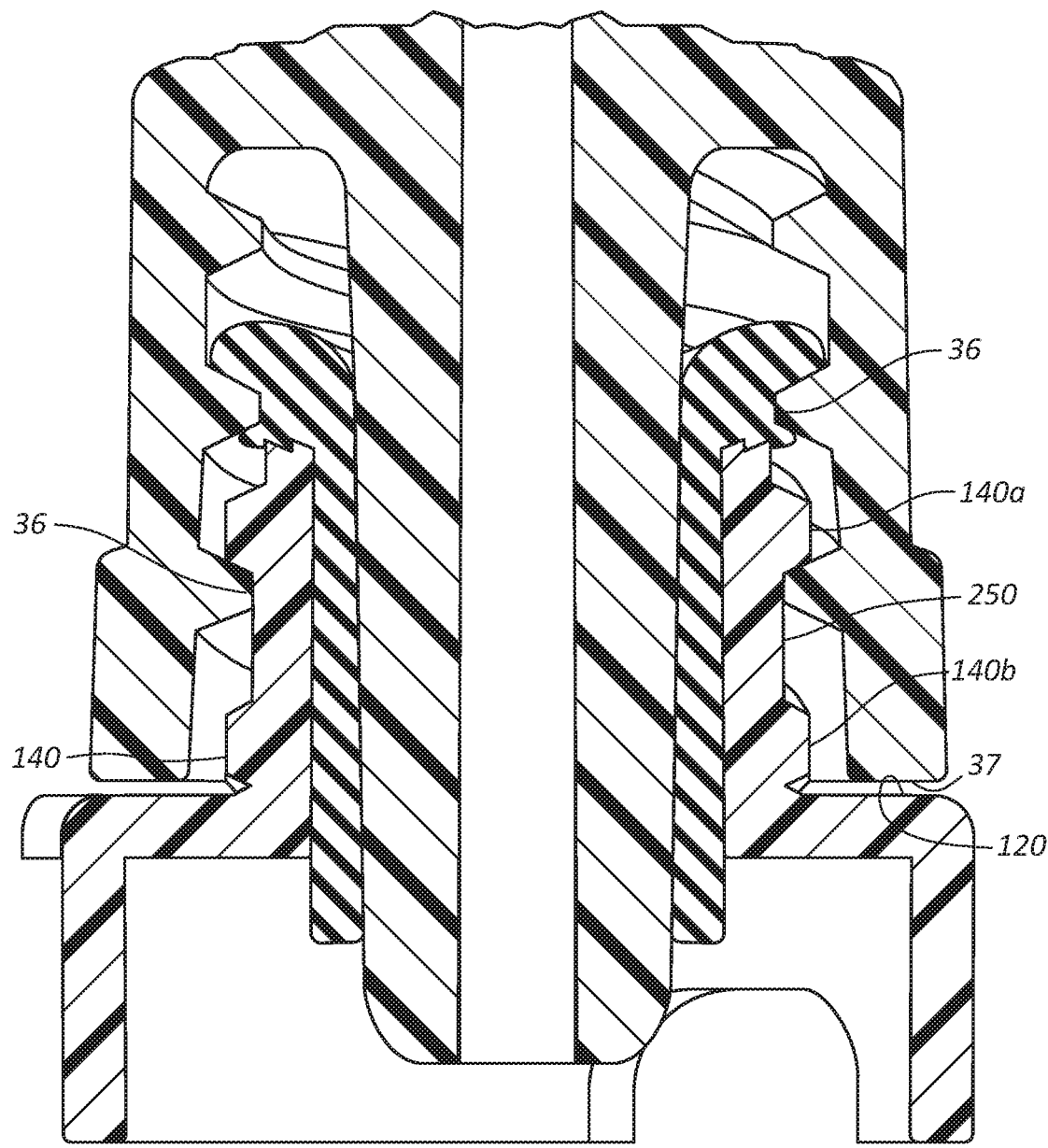
FIG. 5B is another cross-sectional view of the tapered retention feature of FIG. 4, according to some embodiments.

Referring now to FIGS. 5A and 5B, various cross-section views are provided which demonstrate the interaction between complementary threads 36 of separate device 26 and tapered retention feature 250. As separate device 26 is threadedly coupled to Luer access device 100, the underside of complementary threads 36 is initially supported by a top surface of threads 140, as shown in FIG. 5A. Upon further coupling or threading of the devices, contact is made between the terminal end 37 of separate device 26 and body 120 of Luer access device 100, thereby preventing further insertion of probe 138 through septum 122, as shown in FIG. 5B. In at least some embodiments, contact between complementary threads 36 and tapered retention feature 250 occurs at or before the initiation of contact between terminal end 37 and body 120.

Upon further rotation of separate device 26, complementary threads 36 are rotated with respect to the fixed position of body 120 and threads 140. The pitch of complementary threads 36 causes the rotating complementary threads 36 to travel upwardly across retention feature 250, such that a top surface of complementary threads 36 contacts a bottom surface of upper threads 140a. As complementary threads 36 travels across retention feature 250, the outward taper of retention feature 250 increases resistance between complementary threads 36 and retention feature 250. This increased resistance provides a desired tactile sensation to the user which indicates that the connection between the devices is progressively tightening. When the top surface of complementary threads 36 is fully seated against the bottom surface of threads 140, and terminal end 37 is contacting body 120, the connection between the devices 100 and 26 is complete and the user is no longer able to further rotate and/or tighten the connection. The interaction between complementary threads 36 and retention device 250 maintains the tightened connection, thereby preventing any "spring back" effect.

Figure 6A:
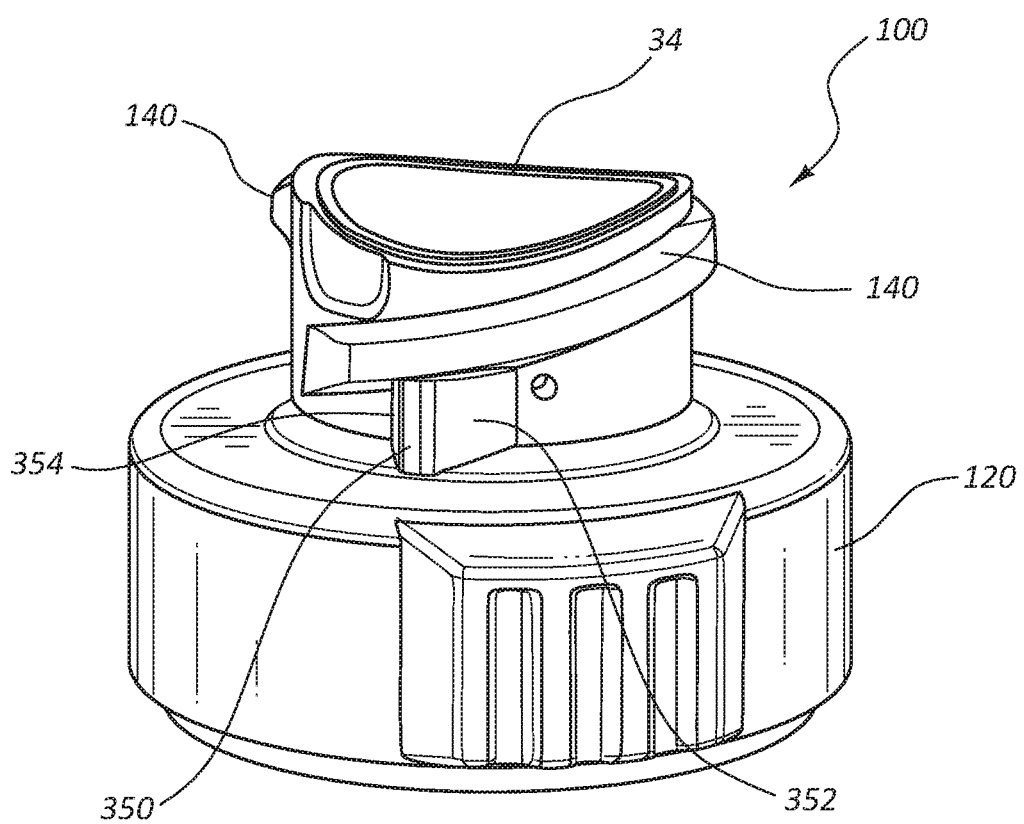
FIG. 6A is an upper perspective view of a Luer access device having an asymmetrical narrow bump retention feature in accordance with a representative embodiment of the present invention.
Figure 6B:
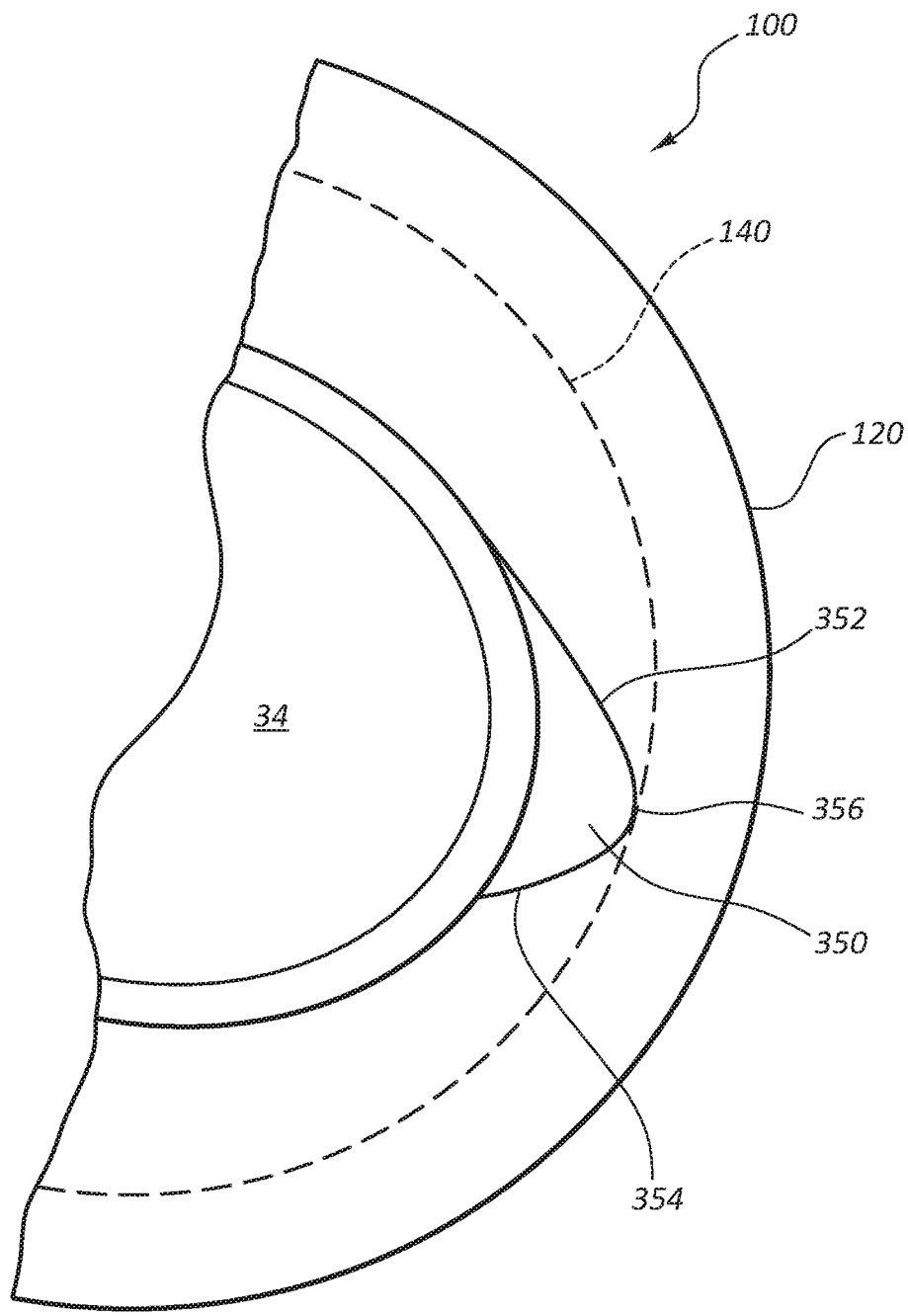
FIG. 6B is a cross-sectional view of a portion of the Luer access device of FIG. 6A, in accordance with a representative embodiment of the present invention.

The present invention may comprise any number of retention features, having any variety of size, shape and features in harmony with the teachings herein. For example, with reference to FIGS. 6A-6C, some implementations of the present invention comprise a retention feature 350 comprising an asymmetric bump having various axial ramps to assist in tightening and loosening the connection between Luer access device 100 and separate device 26.

In some instances, retention feature 350 comprises a forward ramped surface 352 having a shallow, inclined pitch. The force required to pass complementary threads 36 over retention feature 350 increases gradually as complementary threads 36 travel over the inclined ramped surface 352. Retention feature 350 further comprises rearward ramped surface 354 which is opposite forward ramped surface 352 and includes a steep, declined pitch.

Figure 6C:
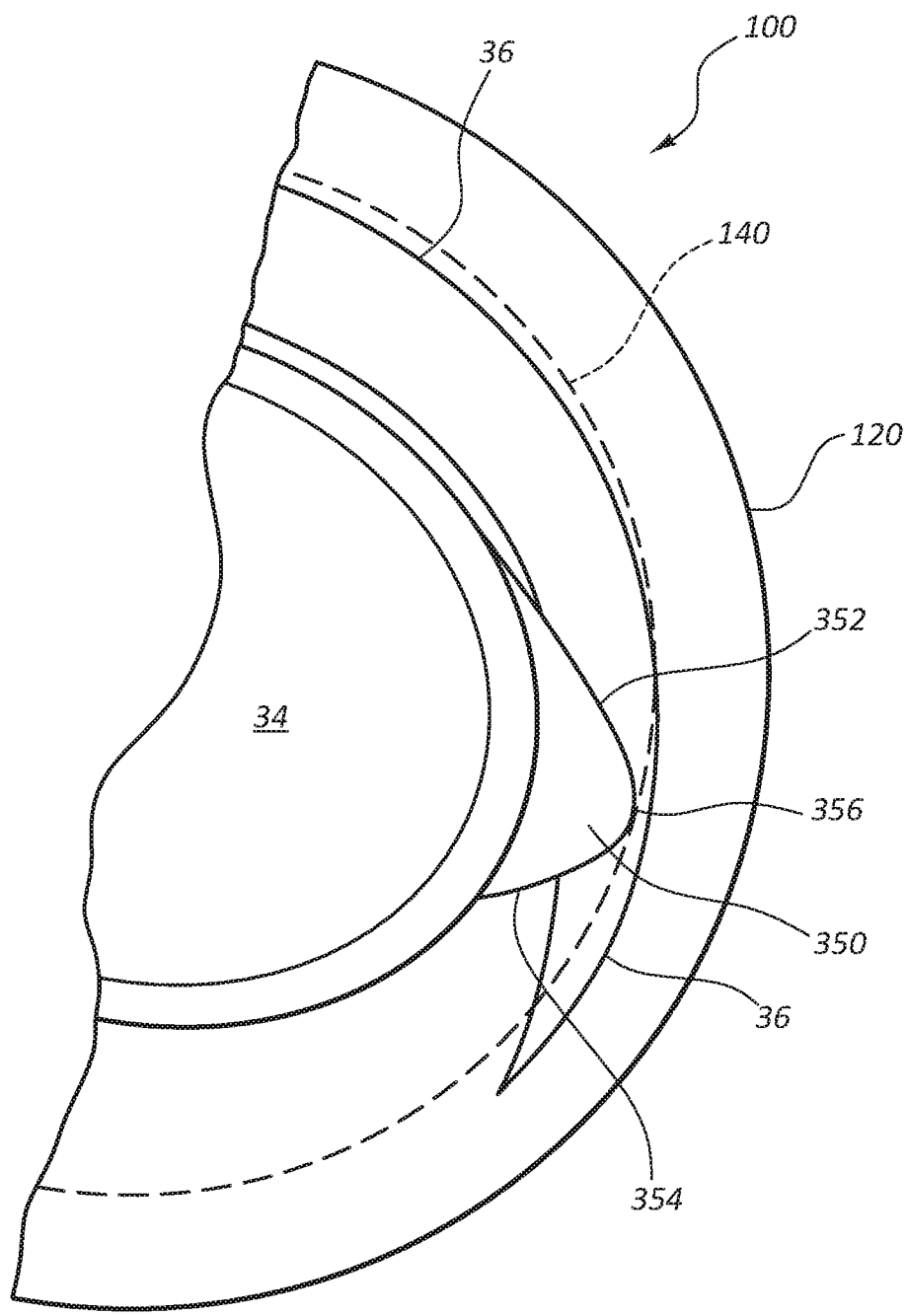
FIG. 6C is another cross-sectional view of a portion of the Luer access device of FIG. 6A, in accordance with a representative embodiment of the present invention.

In some instances, complementary threads 36 comprise a compliant material that temporarily deforms when contacted by retention feature 350. As such, when threadedly coupling complementary threads 36 to threads 140, a portion of complementary threads 36 in contact with retention feature 350 gradually and temporarily deforms as the threads 36 travel up forward ramped surface 352 and over the apex 356 of retention feature 350. As the portion of complementary threads 36 passes over apex 356 and past rearward ramped surface 354, the threads 36 are restored to their original form. Thus, the sections of complementary threads 36 not in contact with retention feature 350 are undeformed, while those sections of complementary threads 36 in contact with retention feature 350 are deformed, as shown in FIG. 6C.

The interface between complementary threads 36 and the steeper pitch of rearward ramped surface 354 requires increased torque for disengaging or unthreading complementary threads 36 from threads 140, as compared to the torque required to threadedly engage threads 36 and 140 based on the shallower pitch of forward ramped surface 354. This feature prevents unintentional disengagement of separate device 26 from Luer access device 100. Further, the steeper pitch and shorter length of rearward ramped surface 354 allows quick disengagement of complementary threads 36 from retention feature 350 once the required torque has been applied and the interface between complementary threads 36 and rearward ramped surface 354 has been released.

Figure 7A:
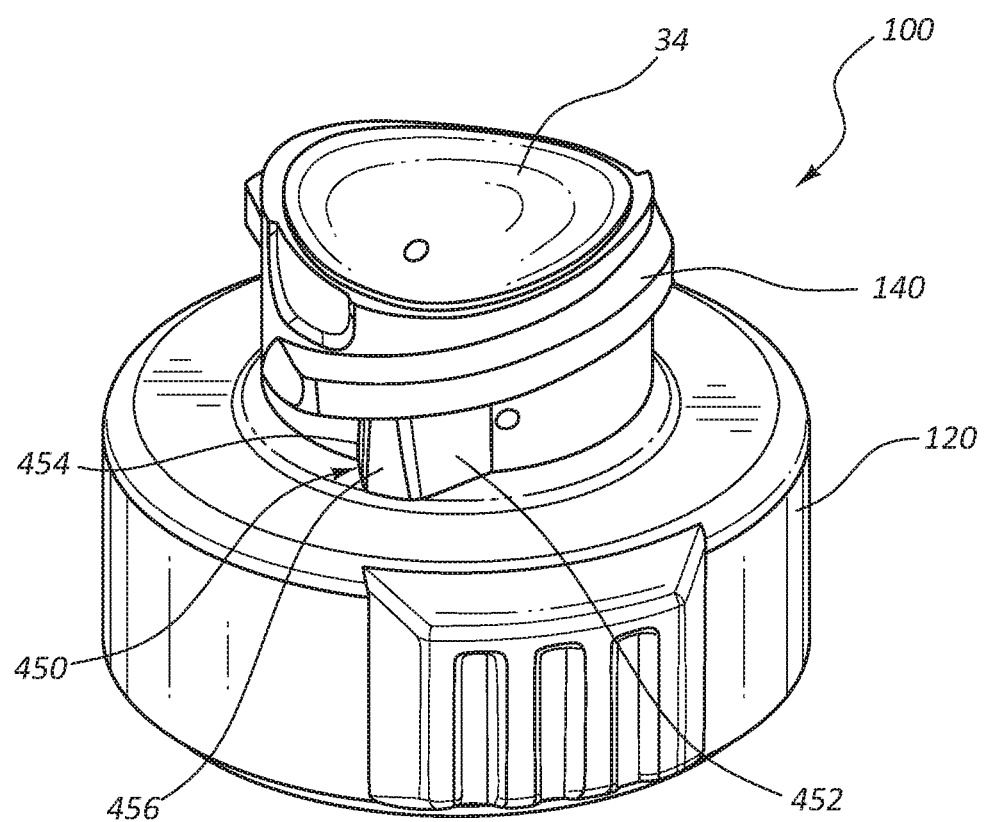
FIG. 7A is an upper perspective view of a Luer access device having an asymmetrical wide bump retention feature with an axial taper in accordance with a representative embodiment of the present invention.
Figure 7B:
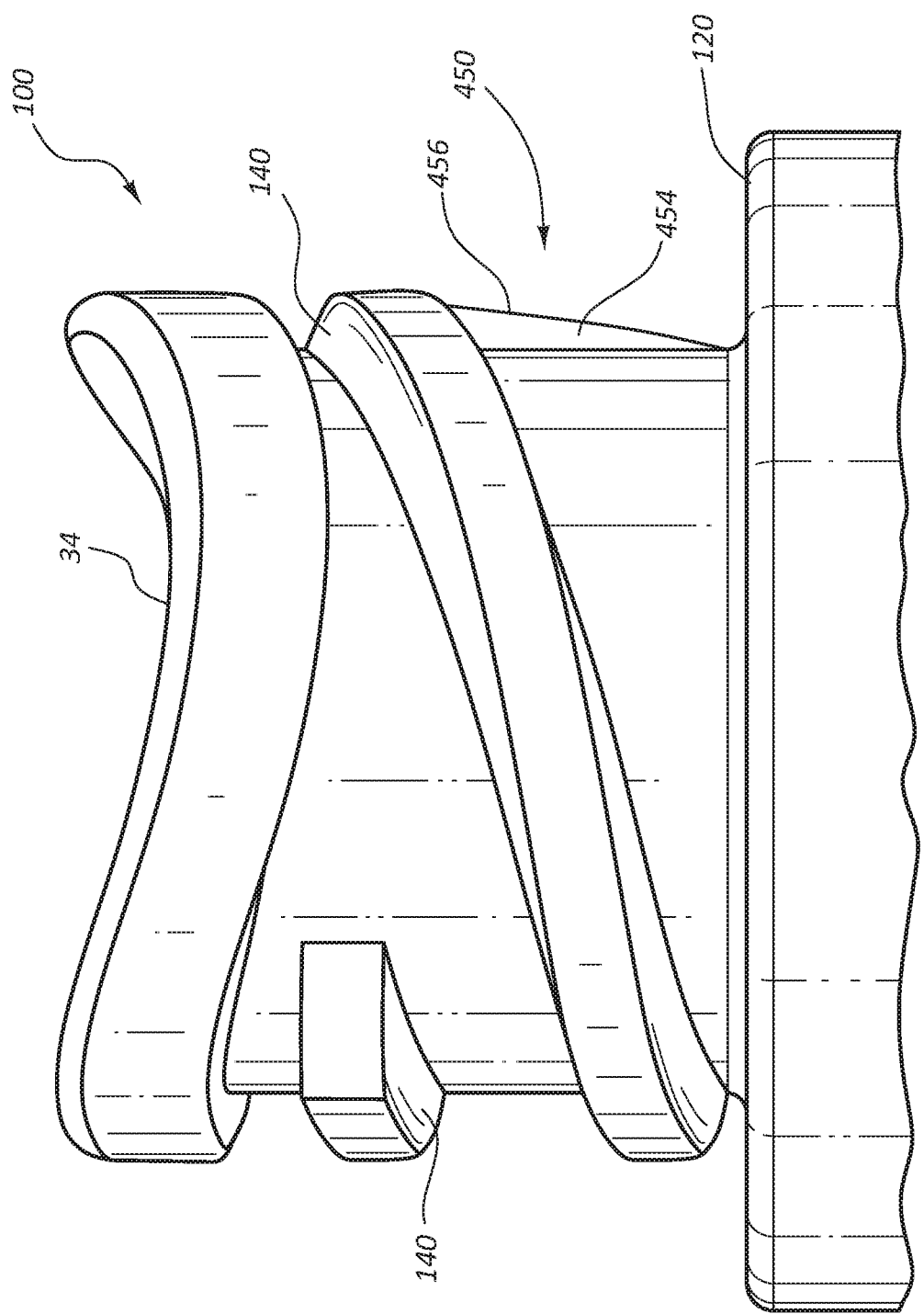
FIG. 7B is a side view of a portion of the Luer access device of FIG. 7A, in accordance with a representative embodiment of the present invention.
Figure 7C:
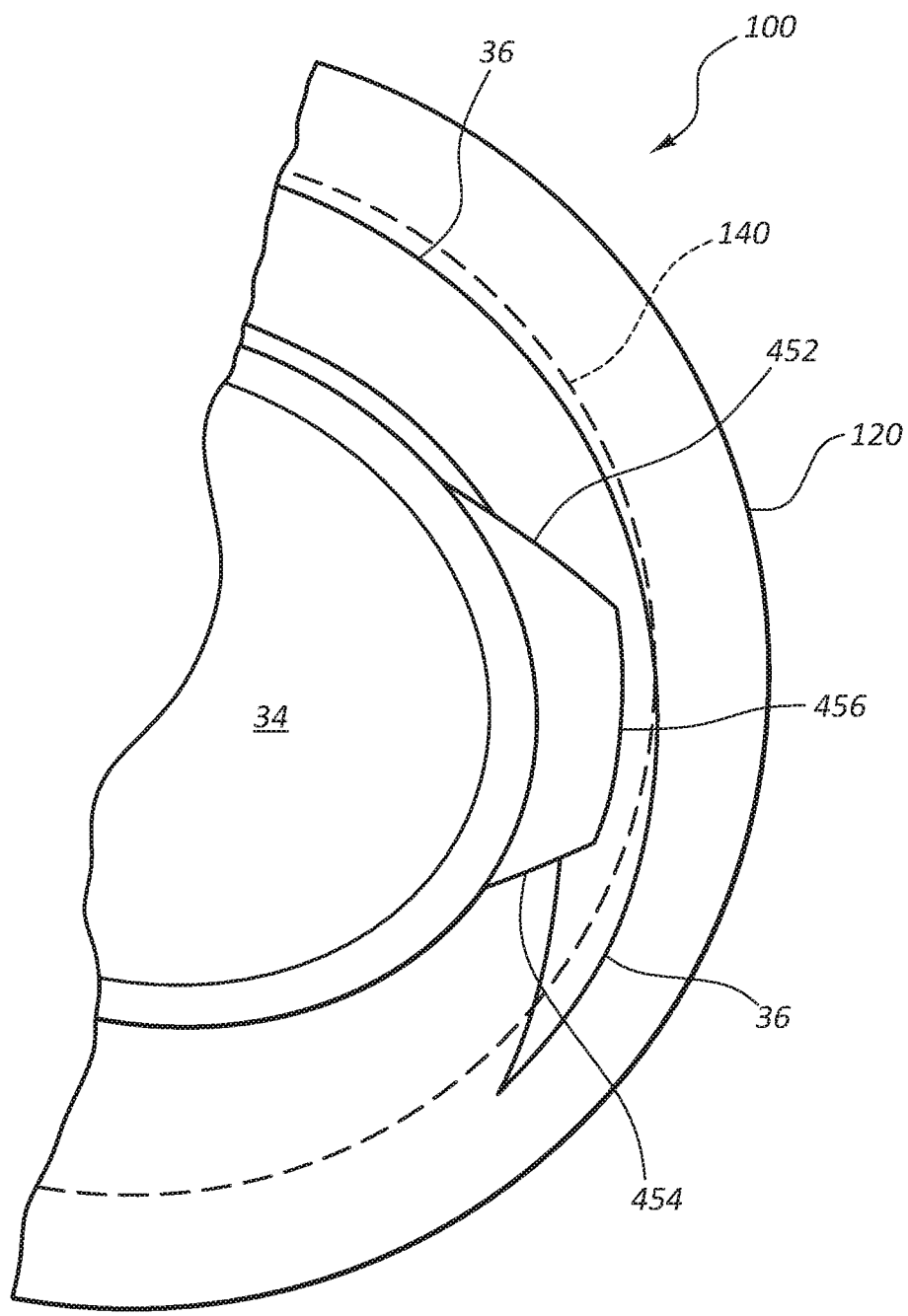
FIG. 7C is a cross-sectional view of a portion of the Luer access device of FIG. 7A, in accordance with a representative embodiment of the present invention.

In some instances, Luer access device 100 further comprises a retention feature 450 having an asymmetrical wide bump 456 comprising an axial taper, wherein the wide bump 456 further comprises a shallow forward ramp 452 and a steep rearward ramp 454, as shown in FIGS. 7A-7C. Forward and rearward ramps 452 and 454 provide benefits similar to those discussed in connection with retention feature 350, above. Wide bump 456 is equivalent to apex 356 of retention feature 350, however the increased width of wide bump 456 increases the interface between retention feature 450 complementary threads 36. As such, the period of resistance between Luer access device 100 and separate device 26 is increased. The increased width of wide bump 456 further increases the length or amount of complementary threads 36 that are deformed by retention feature 450, thereby requiring additional torque to threadedly engage and/or disengage the interconnected devices.

Wide bump 456 further comprises an axial taper, similar to the taper of retention feature 250, shown and discussed above in connection with FIGS. 4A-5B. Thus, as separate device 26 is threaded onto Luer access device 100, complementary threads 36 travel upwardly on the axial taper of wide bump 456, thereby increasing the resistance between complementary threads 36 and retention feature 450. Complementary threads 36 are maximally engaged with threads 140 when an upper thread surface of complementary threads 36 forms an interface with a lower thread surface of threads 140, thereby preventing further rotation of separate device 26. In this position, complementary threads 140 are positioned on wide bump 456 at the maximum width of the axial taper, thereby maximizing the interference between retention feature 450 and complementary threads 36.

Figure 8A:
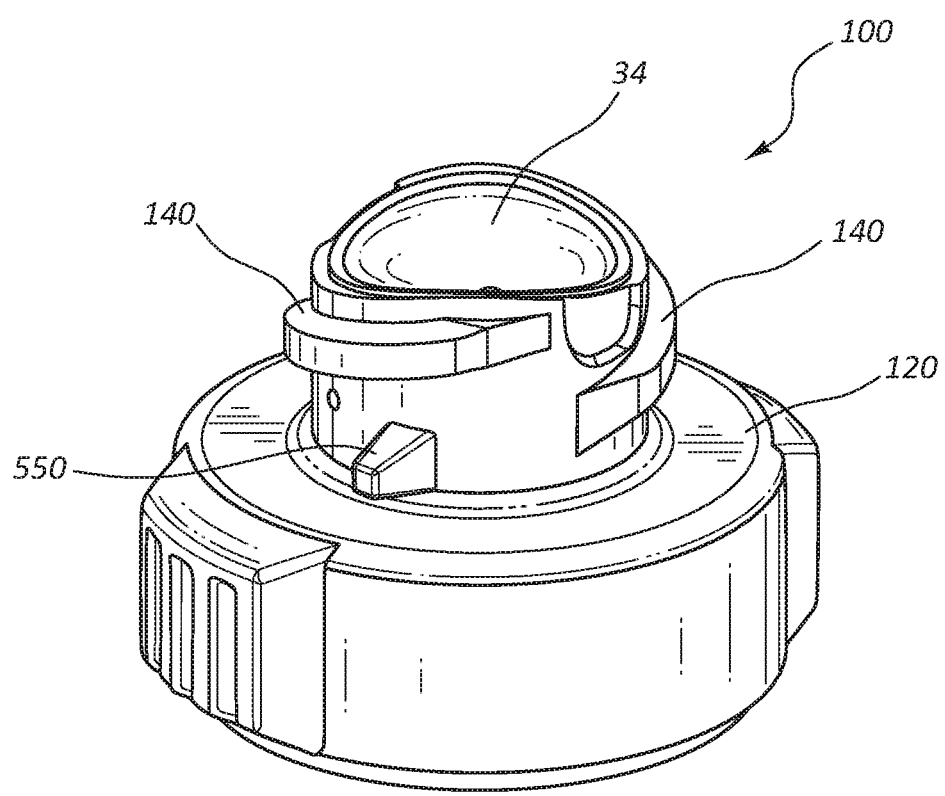
FIG. 8A is an upper perspective view of a Luer access device having a barb retention feature in accordance with a representative embodiment of the present invention.
Figure 8B:
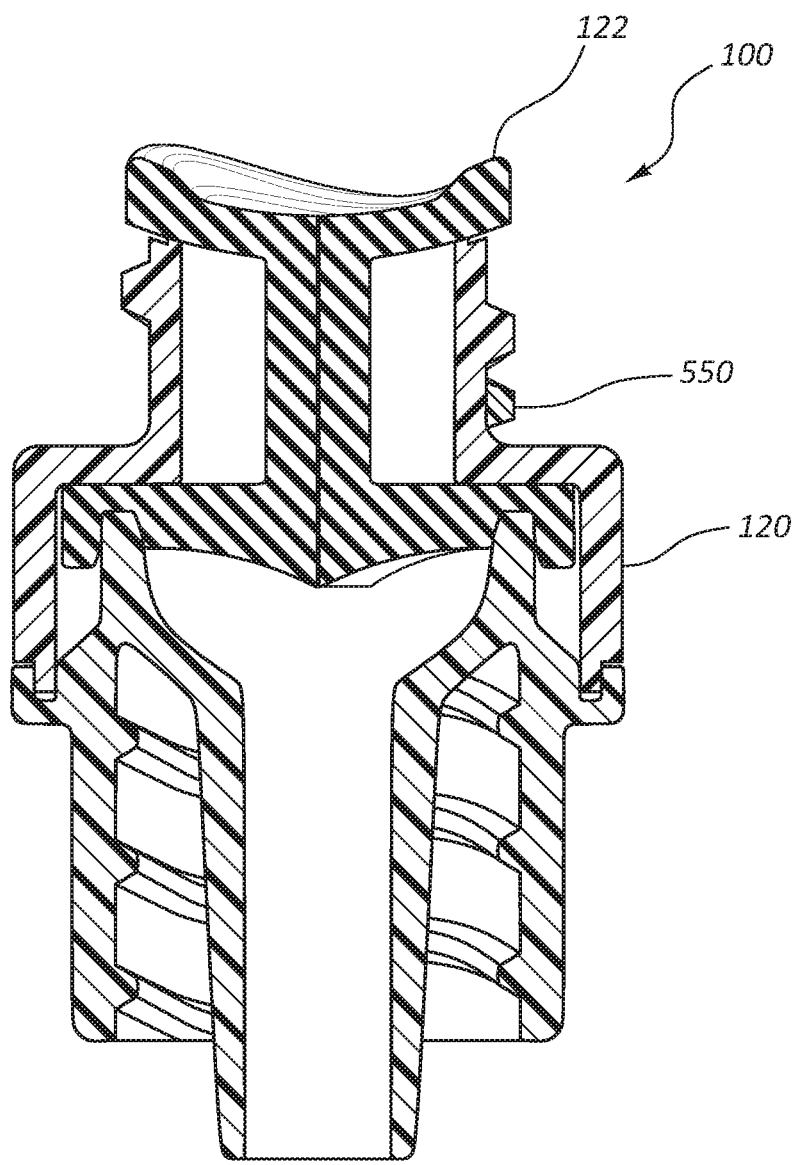
FIG. 8B is a cross-sectional view of the Luer access device of FIG. 8A, in accordance with a representative embodiment of the present invention.
Figure 8C:
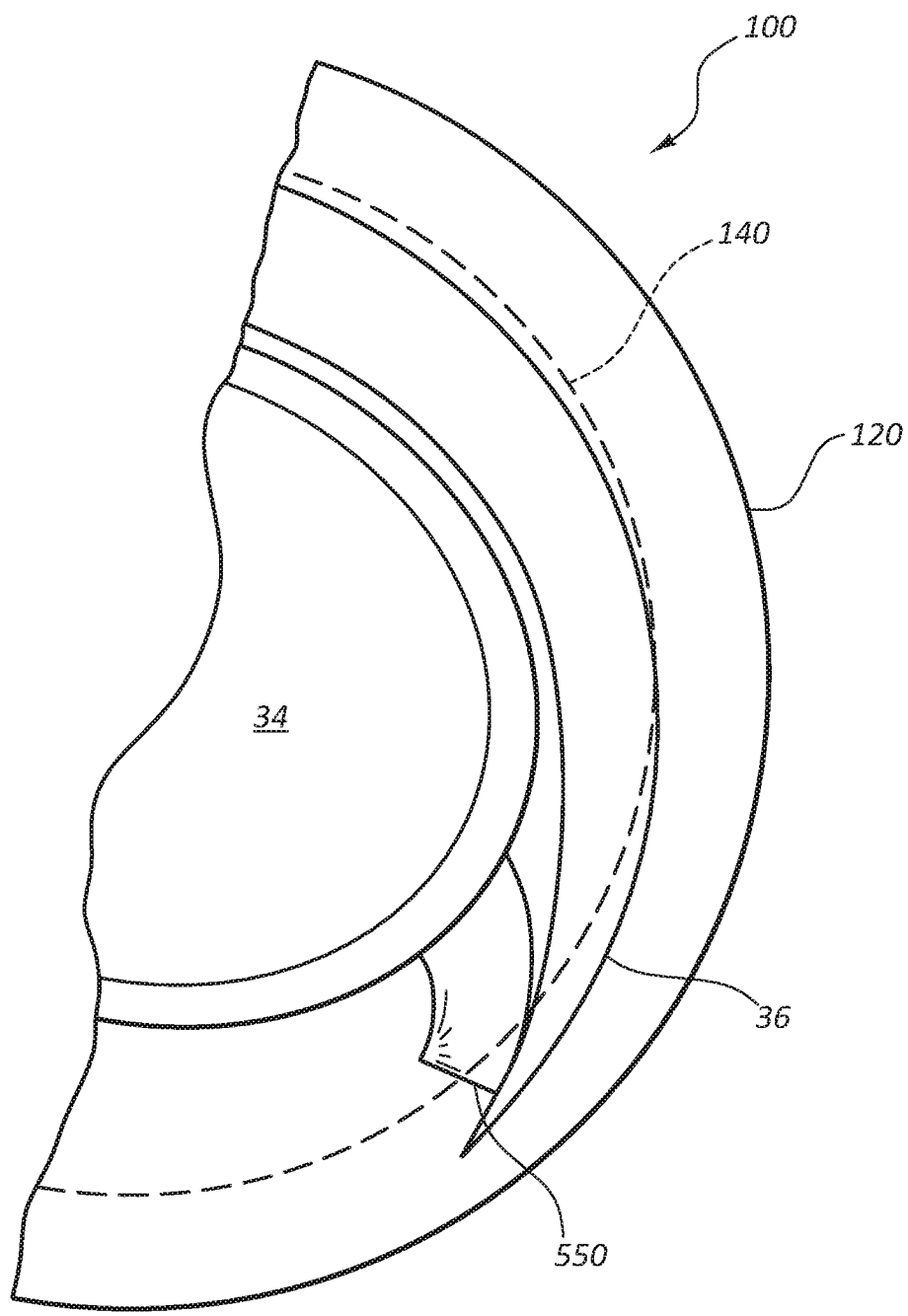
FIG. 8C is another cross-sectional view of the Luer access device of FIG. 8A, in accordance with a representative embodiment of the present invention.

Referring now to FIGS. 8A-8C, some embodiments of the instant invention further include a retention feature 550 comprising a one-way barb. In some embodiments, retention feature 550 comprises a flexible, resilient material and is positioned in the pathway of complementary threads 36, such that complementary threads 36 contact and temporarily displace retention feature 550, as shown in FIG. 8C. In some embodiments, retention feature 550 comprises a wide base and a narrower tip, such that the shear strength of retention feature 550 is less at the tip and greater at the base. Thus, less shear force is required to displace the tip of retention feature 550 than is required to displace the base. As such, the user is provided with a tactile sensation of a gradually tightening connection. In some instances, retention feature 550 comprises tapered sidewalls, such that the shear strength of retention feature 550 progresses linearly from the feature's tip to the base. In other instances, retention feature 550 comprises sidewalls having a configuration to achieve a non-linear progression of shear strength from the tip to the base.

The resilient nature of retention feature 550 applies an outward force on complementary threads 36 when displaced. This outward force provides a tactile sensation to the user which indicates that the threaded connection is tightening. The outward force further increases the torque required to continue advancing the threaded connection. Once fully engaged, the outward force prevents unintentional disengagement of the threaded devices.

When unthreading the devices, the outward force applied by retention feature 550 requires increased torque to overcome the frictional force between complementary threads 36 and retention feature 550. The frictional force between complementary threads 36 and retention feature 550 gradually decreases as the devices are unthreaded due to the tapered configuration of complementary threads 36 and the resilient nature of retention feature 550. At the point in which complementary thread 36 no longer contacts retention feature 550, all frictional force between threads 36 and feature 550 ceases and the amount of torque required to unthread the devices decreases.

Figure 9:
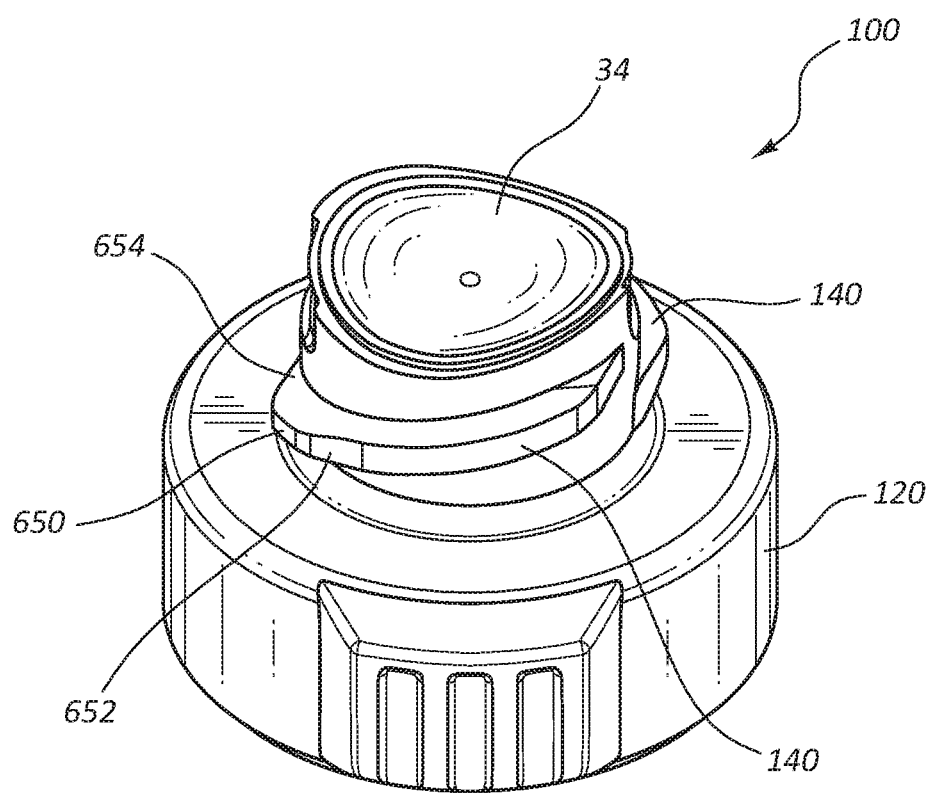
FIG. 9 shows a perspective view of a Luer access device having retention feature forming a portion of a thread in accordance with a representative embodiment of the present invention.
Figure 10:
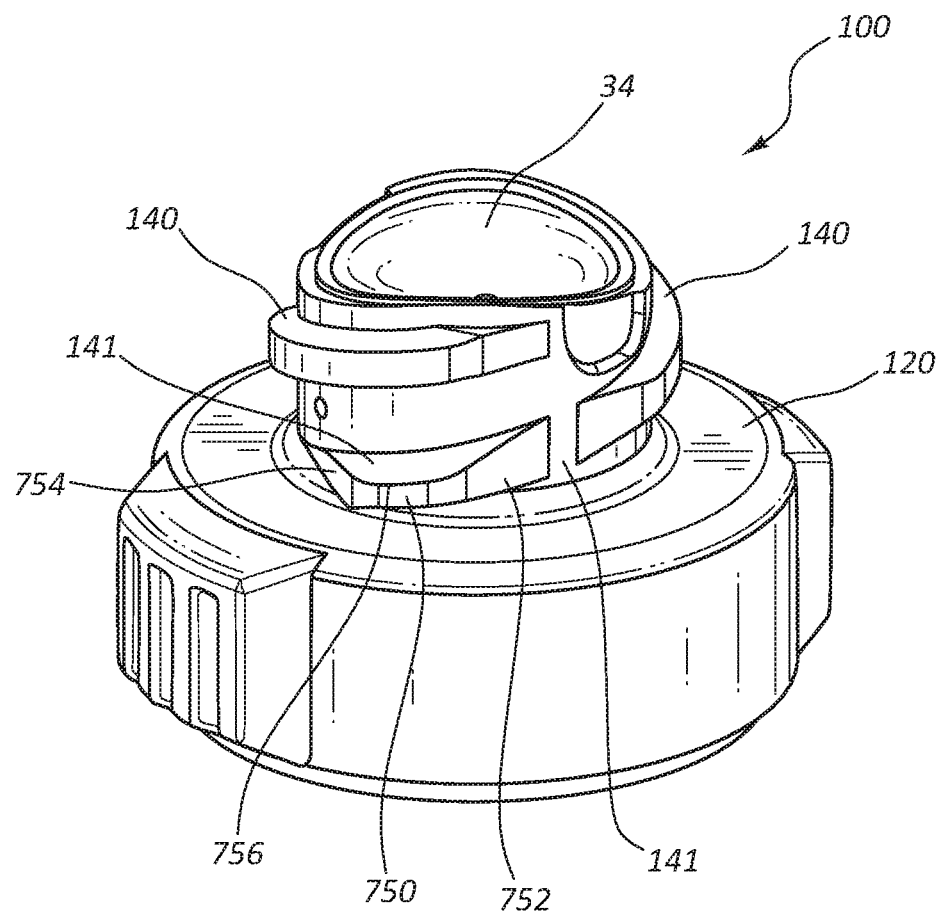
FIG. 10 shows a perspective view of a Luer access device having a retention feature forming a portion of a separate thread in accordance with a representative embodiment of the present invention.

Referring now to FIG. 9, in some embodiments a retention feature 650 is provided as part of threads 140. In this configuration, retention feature 650 interacts with the surface of separate device 26 that is interposed between, or adjacent to complementary threads 36, as opposed to directly interacting with complementary threads 36. For example, retention feature 650 may be designed to engage a major diameter of complementary threads 36, wherein the previous retention feature embodiments are configured to engage the minor diameter of complementary threads 36.

Retention feature 650 may comprise any of the features or elements of the previously discussed retention features. For example, in some instances retention feature 650 comprises a forward ramped surface 652 and a rearward ramped surface 654. Retention feature 650 may further comprise a wide bump surface. In some instances, a Luer access device is provided which comprises two or more retention features, wherein a first retention feature is configured to directly interact with a set of complementary threads, and a second retention feature is configured to interact with a surface of a separate device that is interposed between, or adjacent to the complementary threads.

In some instances, Luer access device 100 includes a retention feature 750 that comprises a portion of a separate thread 140*a*. Thus, a gap 141 is provided between threads 140 and separate thread 140*a*. Retention feature 750 may include any feature or combination of features discussed above in connection with any of the other retention features. In some instances, retention feature 750 comprises wide bump 756 that is tapered radially from the forward ramped surface 752 to the rearward ramped surface 754. Thus, the frictional force between retention feature 750 and the major diameter of complementary threads 36 increases gradually as contact between wide bump 756 and complementary threads is advances.

The present invention may be embodied in other specific forms without departing from its structures, methods, or other essential characteristics as broadly described herein and claimed hereinafter. Thus, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A luer access device, comprising:
 a body having an outer surface;
 an opening formed in the outer surface and configured to receive a needleless connector;
 a soft septum disposed in the opening and having a slit for receiving the needleless connector; and
 a set of threads on the outer surface, wherein a thread of the set of threads comprises a retention feature extending outwardly from the thread, wherein the retention feature is positioned to contact a portion of a complimentary set of threads on the needleless connector when threadedly coupled to the set of threads and provide increased resistance to unintentional disengagement of the threaded devices and a tactile feedback to a user of a tightened connection between the luer access device and the needleless connector, wherein the retention feature comprises a forward ramped surface and a rearward ramped surface, wherein the forward ramped surface is tapered at a first angle of incline along an axis that extends outwardly from the body, wherein the rearward ramped surface is tapered at a second angle of incline along the axis that extends outwardly from the body, wherein the second angle of incline is greater than the first angle of incline, wherein the first angle of incline provides a gradual increase in rotational torque required to threadedly couple the luer access device to the needleless connector.

2. The luer access device of claim 1, wherein the forward ramped surface and the rearward ramped surface converge at an apex generally aligned with a longitudinal axis of the body.

3. The luer access device of claim 1, wherein the thread is separate from another thread of the set of threads.

* * * * *